(12) United States Patent
End et al.

(10) Patent No.: US 8,575,394 B2
(45) Date of Patent: Nov. 5, 2013

(54) PREPARATION OF ALPHA-HYDROXYKETONES

(75) Inventors: Nicole End, Oberwil (CH); Reinhard H. Sommerlade, Neuenburg am Rhein (DE); Yvonne Richter, Zell im Wiesental (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/557,281

(22) Filed: Jul. 25, 2012

(65) Prior Publication Data

US 2012/0289721 A1 Nov. 15, 2012

Related U.S. Application Data

(62) Division of application No. 11/631,448, filed as application No. PCT/EP2005/053060 on Jun. 29, 2005, now Pat. No. 8,252,959.

(30) Foreign Application Priority Data

Jul. 8, 2004 (EP) .................................... 04103236

(51) Int. Cl.
*C07C 225/00* (2006.01)
*C07C 223/00* (2006.01)

(52) U.S. Cl.
USPC .......................................... 564/343; 564/342

(58) Field of Classification Search
USPC .......................................... 564/342, 364, 343
See application file for complete search history.

(56) References Cited

U.S. PATENT DOCUMENTS

| | | | |
|---|---|---|---|
| 3,082,255 A | 3/1963 | Stevens et al. | 260/570.5 |
| 3,455,967 A | 7/1969 | Hatch | 260/348 |
| 4,146,453 A | 3/1979 | Via | 204/159.23 |
| 4,308,400 A | 12/1981 | Felder et al. | 568/336 |
| 4,988,829 A | 1/1991 | Fiedler et al. | 549/519 |
| 5,750,740 A | 5/1998 | Jones et al. | 549/519 |
| 2003/0236419 A1 | 12/2003 | Wang et al. | 548/267.8 |

FOREIGN PATENT DOCUMENTS

| EP | 0 094 726 | 11/1983 |
|---|---|---|
| GB | 1156042 | 6/1969 |

OTHER PUBLICATIONS

Hawley, The Condensed Chemical Dictionary, 1971, Van Nostrand Reinhold Co.8th ed. p. 802-803, (pp. 4).*
Journal of Organic Chemistry vol. 34, No. 7, Jul. 1969, pp. 2133-2137.
Chemical Abstracts No. 1995: 788654
L. Fieser, Journal of American Chemical Society, vol. 75, 1953, pp. 4387-4394.
D. Villemin et al., Synthetic Communications, vol. 25(20), 1995, PP. 3141-3144.
P. Laszlo, Science vol. 235(4795), 1987, pp. 1473-1477.
Chemical Abstracts No. 1969:524684.
M.S. Carson et al.; Journal of the Chemical Society: Organic (1969), 16, pp. 2220-2223.
Database Beilstein XP002311098.
N. Ismail et al.; Chemistry Letters 2000, The Chemical Society of Japan, pp. 844-845.
Trost et al., Tetrahedron Letters, vol. 25, No. 2, 1984, pp. 173-176.
M. Khuddus et al.; Journal of American Chemical Society vol. 95 No. 25, 1973, 8393-8402.
T. Tsuji; Tetrahedron Letters No. 22, 1966, pp. 2413.
A. Steinreiber et al.; Tetrahedron: Asymmetry 12 (2001), pp. 1519-1228.
S. Antoniotti et al.; Synthesis 2003 (18), pp. 2753-2762.
R. Neville et al, Journal of Applied Polymer Science vol. 11, pp. 2029-2036 (1967).
R. Anderson et al, Journal of American Chemical Society, vol. 97, 4327-4333 (1975).
Beilstein XP-002321297.
English Language abstract from the esp@cenet printed on Feb. 9, 2007 of EP 0 094 726.
Noemi, Garcia-Delgado et al., Tetrahedron: Asymmetry, vol. 15, (2004), pp. 2085-2090.
C. Stevens et al, Journal of Organic Chemistry, vol. 27, (1962), pp. 4392-4396.

* cited by examiner

*Primary Examiner* — Taylor Victor Oh
(74) *Attorney, Agent, or Firm* — Shruti Costales

(57) ABSTRACT

A process for the preparation of an 1,1-disubstituted oxirane is disclosed, wherein an organic sulphide is reacted in a polar solvent with an educt containing a leaving group attached to a primary or secondary carbon atom, and/or the sulfonium salt formed in this way is reacted with a ketone in presence of a base and a polar solvent. Oxiranes of the type obtained may be further converted into the corresponding α-hydroxyketone or α-aminoketone, either in one step by subjecting to aerobic oxidation in the presence of a transition metal catalyst, or in two steps by hydrolyzation in the presence of an aqueous acid to the corresponding dialcohol and subsequent selective oxidation. Further described are some novel epoxide intermediates. The α-hydroxyketones and α-aminoketones thus obtainable are useful inter alia as photoinitiators.

7 Claims, No Drawings

PREPARATION OF ALPHA-HYDROXYKETONES

This is a divisional application of the U.S. patent application Ser. No. 11/631,448, field Jun. 10, 2008, now U.S. Pat. No. 8,252,959 which is the national phase application of PCT/EP2005/053060, filed Jun. 29, 2005.

The present invention relates to a process for the preparation of an 1,1-disubstituted oxirane, its oxidative opening in one or two reaction steps with formation of an α-hydroxyketone or α-aminoketone, and to some novel epoxide intermediates.

Compounds of the α-hydroxyketone class may be employed in many technical fields, one of them being the initiation of chemical reactions on irradiation.

Oxiranes or epoxides are 3-membered rings comprising 2 carbon atoms and 1 oxygen atom. Preparation of certain substituted oxiranes by reaction of a carbonyl compound with a sulphur-ylide is described in U.S. Pat. No. 3,455,967.

Known oxidation reactions of epoxides, some of them yielding α-hydroxyketones, are compiled for example in Synthesis 2003, No. 18, pp. 2753-2762. Conversion to α-hydroxyketones usually requires several steps, high amounts of reagents or catalysts.

SUMMARY OF THE INVENTION

It has now been found that an arylmethyl sulphonium salt capable of building a sulphur-ylide may conveniently and in good yield be converted into an epoxide by reaction with a ketone and a base in presence of a polar solvent.

The sulphonium salt may conveniently be prepared in situ by reacting a suitable organic sulphide in a polar solvent with an educt wherein a leaving group is attached to a primary or secondary carbon atom.

The epoxide may conveniently be converted into the desired hydroxyketone or aminoketone by methods known in the art. A further finding of the invention is that, surprisingly, a single reaction step may lead to the desired end product in an even more convenient manner by catalytic opening with aerobic partial oxidation.

The following scheme summarizes an example of the present invention:

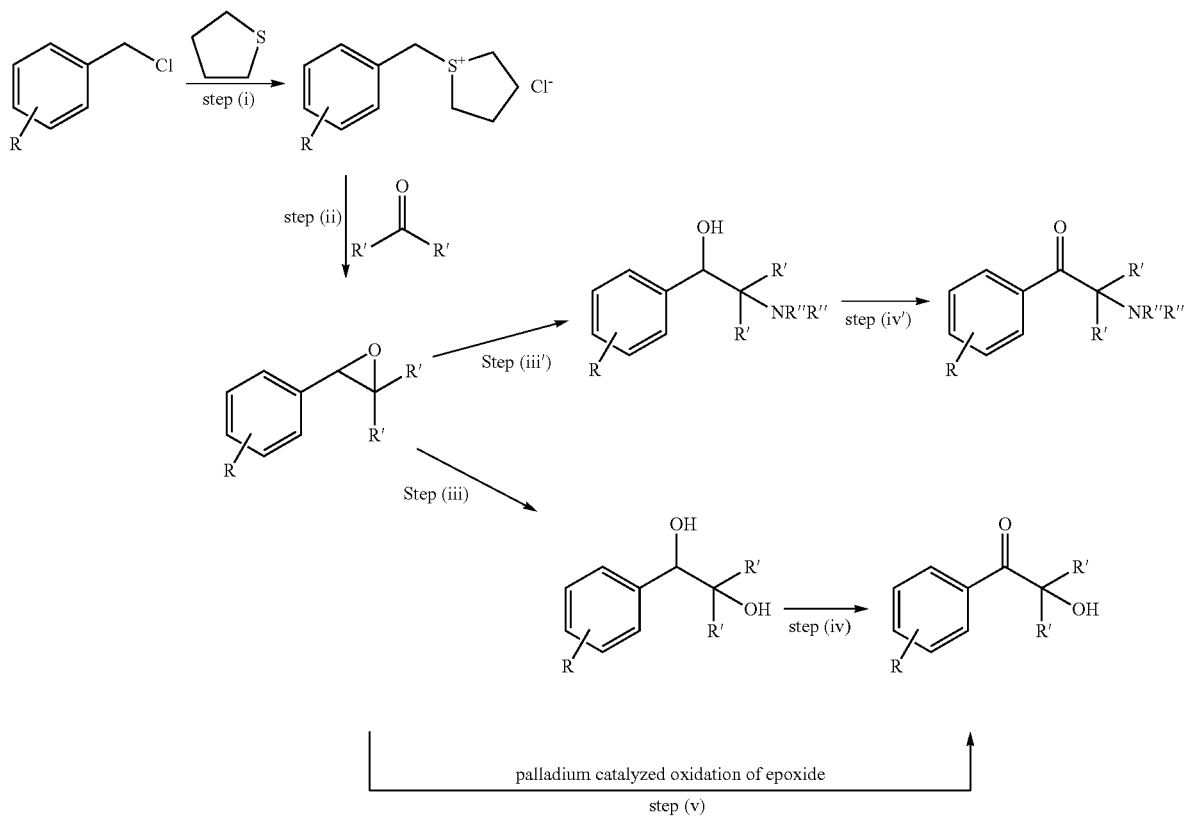

where inter alia each of R and R" may denote hydrogen or hydrocarbyl such as alkyl, and R' is hydrocarbyl such as alkyl.

Preparation of the Epoxide

Thus, the present invention includes a process for the preparation of an 1,1-dicarbo substituted epoxide, which process comprises i) reacting a suitable organic sulphide in a polar solvent with an educt wherein a leaving group is attached to a benzylic moiety, and reacting the product ii) with a ketone in presence of a base and a polar solvent.

Suitable organic sulphides, also recalled as thio ethers, include dialkyl sulphides, alkyl-aryl sulphides and alkyl-cycloalkyl sulphides. Preferred sulphides conform to the formula: R—S—R', wherein R is alkyl, e.g. of 1 to 20 carbon atoms, which is unsubstituted or substituted by $C_5$-$C_{12}$cycloalkyl or phenyl, and R' is as defined for R or is $C_5$-$C_{12}$cycloalkyl, phenyl, phenyl substituted by $C_1$-$C_{12}$alkyl; or R and R' together are penta- or hexamethylene, which may be substituted by $C_1$-$C_{12}$alkyl or phenyl. Most preferred sulphides are ($C_1$-$C_4$alkyl)$_2$S such as dimethyl sulphide, tetrahydrothiophene, or a sulphide $A_1CH_2$—S—$CH_2A_1$, where $A_1$ is the same as used in the educt explained below.

Advantageously, the sulphide is recovered after step (ii) and used again for another batch of step (i) or is, in case of a continuous reaction, reentered into the system before step (i).

In step (i), the educt wherein a leaving group is attached to a benzylic moiety usually is of the formula X

$$A_1\text{-}CH_2\text{—}X \quad (X)$$

wherein X is the leaving group, preferably selected from halogen, OH, OAc, wherein halogen usually is I, Br or Cl and Ac stands for an acyl residue of a suitable carboxylic or preferably sulphonic acid such as toluene sulphonic acid (tosyl), bromophenylsulphonic acid (brosyl), nitrophenylsulphonic acid (nosyl), trifluoromethylsulphonic acid, and $A_1$ is as defined below.

Reaction step (i) is preferably carried out with heating, e.g. at a temperature ranging from 25° C. to reflux temperature, e.g. between 30 and 150° C., preferably between 50 and 120° C.

Organic sulphide and leaving group in the benzylic educt are often employed in about equimolar amounts, e.g. 0.7 to 1.5, preferably 0.9 to 1.1 equivalents of organic sulphide on one equivalent of leaving group.

In reaction step (i), frequently a non-polar solvent is used concomitantly, e.g. an aliphatic or aromatic hydrocarbon or mixture of such solvents such as toluene, xylene, petrol ether etc. This usually results in the formation of a 2 phase system in the beginning of the reaction, which may turn into a 1 phase system with increasing amount of sulphonium salt formed. A phase transfer catalyst may be added but usually is not required. Mixing during the reaction is usually effected by stirring and/or refluxing.

The sulphonium salt formed in step (i) may conform to the formula:

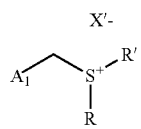

wherein R is alkyl, e.g. of 1 to 20 carbon atoms, which is unsubstituted or substituted by $C_5$-$C_{12}$cycloalkyl or phenyl, and R' is as defined for R or is $C_5$-$C_{12}$cycloalkyl, phenyl, phenyl substituted by $C_1$-$C_{12}$alkyl; or R and R' together are penta- or hexamethylene, which may be substituted by $C_1$-$C_{12}$alkyl or phenyl; $A_1$ is as defined below; and X'- is a suitable anion, e.g. the anion of the leaving group of the compound of formula X such as halogenide, hydroxyl, acylate etc., or another suitable anion such as sulfate, hydrogensulfate, $BF_4^-$, $PF6^-$ (introduced, for example, by ion exchange). Advantageously, the sulphonium salt formed in step (i) is not isolated, and the reaction mixture is used for step (ii) without further purification or other treatment.

Naturally, it is also possible to start the present process using the sulphonium salt from any source, and reacting it with a ketone and a base in presence of a polar solvent. In this case, reaction conditions are as described for step (ii) of the process of the invention.

Surprisingly, the reaction of ketone and sulphonium salt obtained in step (i) under the present condition clearly dominates over 2 important competing side reactions, i.e.
1. the aldol condensation of the ketone and
2. base-induced rearrangement of the sulphonium salt with alkylation of the aromatic ring. Thus, pre-mixing of ketone and base as well as pre-mixing of sulphonium salt and base becomes possible, and the reaction proceeds immediately after completion of the reaction mixture, yielding the desired epoxide in good yield. Of course, other sequences are possible, such as mixing of the product from step (i) with ketone followed by addition of the base.

Preferred polar solvents in both steps (i) and (ii) are selected from water, alcohols such as methyl, ethyl or propyl alcohol, or mixtures of these solvents.

Typically, polar solvents in step (i) include water, alcohols such as methyl, ethyl or propyl alcohol, ketones or sulphides, such as the sulphide used as educt in step (i), or mixtures of these solvents such as alcohol-water mixtures. Most preferred polar solvent is water.

Typical polar solvents in step (ii) include water, alcohols such as methyl, ethyl or propyl alcohol, ketones, such as the ketone used in the reaction step (ii), sulphides, mixtures of these solvents such as alcohol-water mixtures, or mixtures of one or more of these polar solvents with a cosolvent selected from aromatic solvents such as benzene, toluene, xylene, and ethers. More preferred are water, alcohols or mixtures thereof, or mixtures of one or more of these polar solvents with a cosolvent as given above, where the volume ratio cosolvent:polar solvent is smaller than 2:1, especially smaller than 1:1.

Most preferred polar solvent in step (ii) is an alcohol such as a $C_1$-$C_4$alkohol, especially methanol, ethanol.

Reaction step (ii) is preferably carried out at a temperature ranging from about −10° C. to about 50° C., e.g. between 0 and 40° C., preferably at about room temperature or below 25° C.

Preferred base is a metal hydroxyde, mainly an alkaline hydroxide such as LiOH, NaOH, KOH or mixtures thereof. Most preferred is NaOH. The base is preferably used as a concentrated solution (e.g. 20-50% base by total weight of the solution) in water, alcohol or water/alcohol mixture. The base is usually employed in about equimolar amount or in slight excess, relative to the ketone, for example 0.9 mol-1.5 mol hydroxide on 1 mol ketone.

In a preferred process, the ketone is of the formula $A_2$-CO-$A_3$, where $A_2$ and $A_3$ are as defined below. Examples for preferred ketones include acetone, ethyl methyl ketone, cyclohexanone. The ketone is usually employed in about equimolar amount or in excess, relative to the sulphonium salt present from step (i). The ketone may also be used as a solvent or cosolvent in step (ii), amounts ranging, for example, from 0.9 mol to about 20 mol, preferably from 1 to 10 mol ketone per mol sulphonium salt.

The epoxide obtainable in the present process is a 1,1-dicarbo substituted ethylene oxide (oxirane), for example of the formula

(II')

or of the formula II described further below.

A benzylic educt is used in step (i), which means that the leaving group in said educt is attached to an arylmethyl moiety such as benzyl, which may be unsubstituted or substituted in the phenyl moiety. Consequently, in the educts and products usually employed, $A_1$ is an aromatic organic carbon anchor group, and $A_2$ and $A_3$ each are an organic group containing at least one carbon atom linked to the carbon carrying the oxygen bond. Each of $A_1$ may contain one or more further structures reactive in the above steps (i) or (ii), i.e. methylene-X or methylene-sulphonium, which are converted in the reaction. In a preferred process, $A_1$ in formula X or in the sulphonium salt, and consequently in the product obtained, is an aryl group, which may carry one or more further structures modified in the present reaction, while no such structures are present in $A_2$ and $A_3$.

Each of $A_2$, $A_3$ may also contain one or more further keto structures which are converted in the reaction.

In a more preferred process, the 1,1-dicarbo substituted oxirane is a compound of the formula II

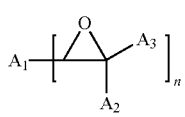

(II)

wherein $A_1$, if n is 1, include carbocyclic aryl which is unsubstituted or substituted by OPr, $NR_9R_{10}$, carboxy, $COR_1$, $SO_2R_2$, halogen, nitro, CN, Aro, and/or by alkyl, alkoxy, alkenyl or alkenyloxy, each of which itself is unsubstituted or substituted by OPr, halogen, $NR_9R_{10}$, carboxy, Aro, $COR_1$, $SO_2R_2$, nitro, CN; or is carbocyclic aryl substituted by O—$R_8$—O—$SiR_{11}R_{12}R_{13}$; if n is 2, preferred meanings of $A_1$ include Ar—$R_5$—Ar; or is a residue $R_{11}R_{12}Si(O—R_8—O—Ar)_2$; if n is 3, preferred meanings of $A_1$ include a residue $(Ar)_3$—$R_6$; or is a residue $R_{11}Si(O—R_8—O—Ar)_3$; if n is 4, preferred meanings of $A_1$ include a residue $(Ar)_4$—$R_7$.

$A_2$ and $A_3$ preferably are alkyl, alkenyl, cycloalkyl, cycloalkenyl, aryl, alkylaryl, arylalkyl, cycloalkylalkyl, or one of said residues substituted by OPr, $NR_9R_{10}$, carboxy, $COR_1$, $SO_2R_2$, halogen, nitro, CN; and/or, if containing at least 3 carbon atoms, are interrupted in a carbon-carbon single bond by O, $NR_9$, COO, $OCONR_9$, $CONR_9$;

or $A_2$ and $A_3$ together are $C_4$-$C_{11}$alkylene, -oxaalkylene, -azaalkylene or -alkenylene, each of which is unsubstituted or substituted by OPr, $NR_9R_{10}$, carboxy, $COR_1$, $SO_2R_2$, halogen, nitro, CN, and/or by alkyl, alkoxy, alkenyl, alkenyloxy, each of which itself is unsubstituted or substituted by OPr, $NR_9R_{10}$, carboxy, $COR_1$, $SO_2R_2$, halogen, nitro, CN.

In the above definitions, Ar stands for a divalent carbocyclic aryl which is unsubstituted or substituted by OPr, $NR_9R_{10}$, carboxy, $COR_1$, $SO_2R_2$, halogen, nitro, CN, Aro, alkyl, alkoxy; Aro stands for aryloxy which is unsubstituted or substituted by OPr, $NR_9R_{10}$, carboxy, $COR_1$, $SO_2R_2$, halogen, nitro, CN, alkyl, alkoxy, alkenyl, alkenyloxy;

Pr stands for hydrogen or a protecting group;

$R_1$ is hydrogen, OH, alkyl, alkenyl, cycloalkyl, cycloalkenyl, phenyl, alkylphenyl, alkoxyphenyl, alkoxy, alkenoxy, cycloalkoxy, cycloalkenoxy, phenoxy, alkylphenoxy, alkoxyphenoxy;

$R_2$ is OH, alkyl or alkoxy;

$R_3$ is alkyl, alkenyl, cycloalkyl, cycloalkenyl, phenyl, alkylphenyl, alkoxyphenyl;

$R_4$ and $R'_4$ independently are hydrogen, $C_1$-$C_{12}$alkyl or cyclohexyl;

$R_5$, $R_6$ and $R_7$ independently are spacer groups of suitable valency to covalently bond the Ar moieties they are attached to; or $R_5$ is a direct bond;

$R_8$ is a divalent aliphatic or cycloaliphatic residue;

$R_9$ and $R_{10}$ independently are hydrogen, $C_1$-$C_{12}$alkyl, $C_1$-$C_{12}$alkyl substituted by OPr and/or $NR_4R'_4$, $C_5$-$C_{12}$cycloalkyl; or $R_9$ and $R_{10}$ are joined together to form a tetramethylene, pentamethylene, oxatetramethylene or oxapentamethylene moiety;

$R_{11}$ and $R_{12}$ independently are $C_1$-$C_{12}$alkyl or $C_1$-$C_{12}$alkoxy.

Preferably, the product obtained in this process is subsequently converted into an α-hydroxy- or aminoketone, e.g. by methods known in the art or in analogy to such methods, e.g. by suitable hydrolysis or aminolysis methods; especially preferred is the conversion by one of the methods described below.

The epoxide product obtained may be used for the subsequent reactions described below without further purification.

Oxidative Epoxide Opening in 1 Step

It has been found that epoxides, such as those defined above, may conveniently be converted into α-hydroxyketones in a single step (v) using a transition metal catalyst under aerobic conditions.

Thus, present invention also pertains to a process for the preparation of an alpha-hydroxy ketone, characterized in that a 1,1-dicarbo substituted 2-hydro-ethylene oxide is objected to aerobic oxidation in the presence of a transition metal catalyst.

The 1,1-dicarbo substituted ethylene oxide (oxirane) educt is, for example, a compound of the formula

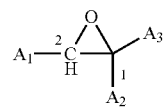

(II')

wherein $A_1$ is hydrogen or an organic carbon anchor group, and $A_2$ and $A_3$ denote the 1,1-dicarbo substituents, each of which, and the organic carbon anchor group $A_1$, if present, are selected from any organic group able to form a carbon-carbon single bond to the carbon atom No. 1 of the oxirane ring, or carbon atom No. 2 in case of $A_1$. Each of $A_1$, $A_2$, $A_3$ may contain one or more further structures of the type 1,1-dicarbo substituted 2-hydro-ethylene oxide which are converted in the reaction. In a preferred process, $A_1$ in formula II' or the below formula II is a carbon anchor group, especially an aryl group, which may carry one or more further structures

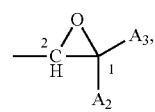

or $A_1$ itself is this structure, to be converted in the present process, while no such structures are present in $A_2$ and $A_3$.

The alpha-hydroxy ketone formed is preferably a compound of the formula I

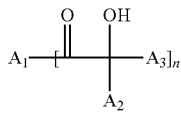

(I)

wherein n ranges from 1 to 4.

The educt preferably is a compound of the formula II

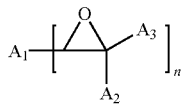

(II)

wherein $A_1$, $A_2$ and $A_3$ and n are as defined above.

Preferably, the reaction is carried out in the presence of water; the transition metal catalyst is mainly selected from those of the metals Pd, Ru, Cu, Fe, Mn, Co, Mo, W, V, Ti, Os, Ta, Pt, usually employed as a metal (oxidation state 0) or in low oxidation state (e.g. I or II), e.g. as a corresponding complex (see below); preferred is a suitable Pd catalyst (e.g. Pd(II)/Pd(0) system).

The transition metal catalyst employed in the present process usually is a complex containing one or more ligands bonded to the transition metal as central atom. In general, ligands may be those described in WO 98/39346 for compounds of formulae I-III explained therein. Preferred are chelating ligands, such as bidentate or tridentate ligands, especially those containing nitrogen. Use of this catalyst for the aerobic oxidation of a 1,1-dicarbo substituted ethylene oxide such as the above compound of formula II is another subject of present invention.

Appropriate monodentate, bidentate and tetradentate neutral $e^-$ donor ligands are derived, for example, from unsubstituted or substituted heteroarenes such as furan, thiophene, pyrrole, pyridine, bipyridine, picolylimine, γ-pyran, γ-thiopyran, phenanthroline, pyrimidine, bipyrimidine, pyrazine, indole, coumarone, thionaphthene, carbazole, dibenzofuran, dibenzothiophene, pyrazole, imidazole, benzimidazole, oxazole, thiazole, dithiazole, isoxazole, isothiazole, quinoline, bisquinoline, isoquinoline, bisisoquinoline, acridine, chromene, phenazine, phenoxazine, phenothiazine, triazine, thianthrene, purine, bisimidazole and bisoxazole. Examples of substituents are OH, halogen, $C(O)OR_{s1}$, $OC(O)R_{s4}$, $C(O)R_{s2}$, nitro, $NH_2$, cyano, $SO_3M_y$, $OSO_3M_y$, $NR_{20}SO_3M_y$, $N=N-R_{s2}$, $C_1$-$C_{12}$alkyl, $C_2$-$C_{12}$alkenyl, $C_1$-$C_{12}$alkoxy, $C_3$-$C_{12}$-cycloalkyl, $C_3$-$C_{12}$cycloalkenyl, $C_2$-$C_{11}$heterocycloalkyl, $C_2$-$C_{11}$heterocycloalkenyl, $C_6$-$C_{10}$aryl, $C_6$-$C_{10}$aryloxy, $C_5$-$C_9$heteroaryl, $C_5$-$C_9$heteroaryloxy, $C_7$-$C_{11}$aralkyl, $C_7$-$C_{11}$aralkyloxy, $C_6$-$C_{10}$-heteroaralkyl, $C_8$-$C_{11}$aralkenyl, $C_7$-$C_{10}$heteroaralkenyl, monoamino, diamino, sulphonyl, sulphonamide, carbamide, carbamate, sulphohydrazide, carbohydrazide, carbohydroxamic acid residue and aminocarbonylamide, in which $R_{s1}$ is hydrogen, $M_y$, $C_1$-$C_{12}$alkyl, $C_2$-$C_{12}$alkenyl, $C_3$-$C_{12}$cycloalkyl, $C_2$-$C_{11}$heterocycloalkyl, $C_6$-$C_{10}$aryl, $C_5$-$C_9$heteroaryl, $C_7$-$C_{11}$aralkyl or $C_6$-$C_{10}$-heteroaralkyl, $R_{s4}$ is hydrogen, $C_1$-$C_{12}$alkyl, $C_2$-$C_{12}$alkenyl, $C_3$-$C_{12}$cycloalkyl, $C_2$-$C_{11}$-hetero-cycloalkyl, $C_6$-$C_{10}$aryl, $C_5$-$C_9$heteroaryl, $C_7$-$C_{11}$aralkyl or $C_6$-$C_{10}$heteroaralkyl, and $R_{s2}$ and $R_{20}$ are hydrogen, $C_1$-$C_{12}$alkyl, $C_2$-$C_{12}$alkenyl, $C_3$-$C_{12}$cycloalkyl, $C_3$-$C_{12}$cycloalkenyl, $C_2$-$C_{11}$hetero-cycloalkyl, $C_2$-$C_{11}$heterocycloalkenyl, $C_6$-$C_{10}$aryl, $C_5$-$C_9$heteroaryl, $C_7$-$C_{11}$aralkyl, $C_6$-$C_{10}$hetero-aralkyl, $C_8$-$C_{11}$aralkenyl or $C_7$-$C_{10}$heteroaralkenyl, and alkyl, alkenyl, alkoxy, cycloalkyl, cycloalkenyl, heterocycloalkyl, heterocycloalkenyl, aryl, aryloxy, heteroaryl, heteroaryloxy, aralkyl, aralkyloxy, heteroaralkyl, aralkenyl and heteroaralkenyl in turn are unsubstituted or substituted by one of the abovementioned substituents; and y is 1 and M is a monovalent metal or y is ½ and M is a divalent metal.

Most preferred ligands are phenanthroline or substituted phenanthroline such as 2,9-dimethylphenanthroline (cuproine), bathocuproine,

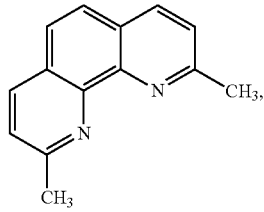

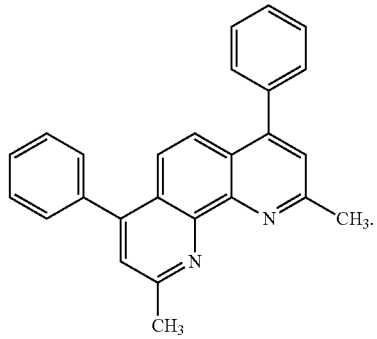

The reaction may be carried out with homogeneous catalysis or heterogeneous catalysis, e.g. by using the transition metal catalyst in immobilized form.

The catalyst may conveniently be prepared in situ from a suitable transition metal salt and a ligand; appropriate salts include halogenides, anions of inorganic oxygen acids or carboxylates, especially acetates.

Water is preferably present in amounts about equivalent to the amount of epoxide in the educt present or in excess, for example in an amount of 0.8 to 100000 mol water per equivalent epoxide, preferably about 1 to 10000, more preferably about 5 to 2000 mol water per equivalent epoxide.

The aerobic oxidation is preferably effected by the presence of gaseous oxygen and/or a molecular oxygen releasing agent. Gaseous oxygen may be applied in the form of pure oxygen or mixtures with other gases, mainly inert gases, such as nitrogen, argon etc.; air is suitable. The pressure is not critical, preferably the reaction is carried out in the range 0.1-300 bar, advantageously at or near atmospheric pressure (e.g. 0.5-3 bar).

As molecular oxygen releasing agent any chemical or mixture may be employed, which is able to release gaseous oxygen; examples are oxo- or peroxo compounds which are decomposed under the conditions of the reaction or after addition of a second component of the agent (e.g. hydrogen peroxide, organic hydroperoxides such as tert.butyl-hydroperoxide, inorganic oxides or peroxides such as manganese (per)oxide, (per)chlorates etc.).

Reaction temperature is advantageously chosen in correlation to the pressure applied, e.g. from the range −10 to 200° C., more preferably 0-150° C., especially 15-110° C.; usually the reaction is carried out with the educt in the liquid state, e.g. using a suitable solvent. The solvent may be water or an organic solvent, preferably miscible with water. Most preferably no further organic solvent is added, e.g. in that way that the reaction is carried out in the presence of water as the only solvent.

Oxidative Epoxide Opening in 2 Steps

Alternatively to the 1-step reaction described above, the conversion of the epoxide into the α-hydroxyketone may also be effected by acidic hydrolysis (iii) followed by selective oxidation (iv). Similarly, aminolysis (iii') followed by selective oxidation (iv') leads to an α-aminoketone.

Thus, the present invention further pertains to the conversion of a 1,1-dicarbo substituted oxirane into an alpha-hydroxy ketone, characterized in that iii) the 1,1-dicarbo substituted oxirane is hydrolyzed in the presence of an aqueous acid to the corresponding dialcohol, iv) and the product obtained is treated with an oxidizing agent selected from hypochlorite, hypobromite, hypervalent iodine reagents.

Advantageously, the dialcohol formed in step (iii) is not isolated, and the reaction mixture is used for step (iv) without further purification or other treatment.

For analogous conversion into the α-aminoketone, step (iii) in the above sequence may be replaced by iii') aminolysis of the 1,1-dicarbo substituted oxirane in the presence of a catalyst to the corresponding alpha-aminoalcohol.

Oxidation of the alcohol function to carbonyl in subsequent step (iv'), optionally after isolation of the desired 1,1-dicarbo-1-amino-2-hydroxy-2-arylethane intermediate, may be effected in analogy to step (iv) described below. Aminolysis in step iii') as well as hydrolysis in step iii) or any isolation, workup or purification step included, may be carried out according to methods known in the art or in close analogy to such methods.

Preferably, the amine used in step iii') is selected from ammonia, primary and secondary amines and corresponding amides such as alkaline amides. Thus, a preferred amine corresponds to the formula V $$YN(R_{18})(R_{19}) \qquad (V)$$

wherein

Y stands for H or an alkali metal, especially Li, Na, K, and $R_{18}$ and $R_{19}$, independently, are selected from H, $C_1$-$C_4$alkyl, or are joined together to form a tetramethylene, pentamethylene, oxatetramethylene, oxapentamethylene, or an azatetramethylene or azapentamethylene moiety, wherein the nitrogen atom is unsubstituted (NH) or is substituted by $C_1$-$C_4$alkyl.

When Y is H, the catalyst may be an acid, e.g. as described for step iii) below. Preferably, a base functions as the catalyst, such as the compound of the formula V itself, or a mixture of such compounds.

In step (iii'), the reaction is preferably carried out in presence of a solvent or an excess of the amine (V) functioning as a solvent. Suirable inert solvents are, for example, aliphatic or aromatic hydrocarbons, e.g. hexane, heptane, octane, liquid hydrocarbon fractions like ligroin or petrol ether, benzene, toluene xylene and the like, amines (e.g. aromatic amines such as pyridine) or ethers. If desired, the reaction may be carried out under pressure, e.g. sufficient for the liquification of the amine used.

Temperature may range, for example, from about −20° C. to reflux, e.g. 0-100° C.

As in the one-step process, the educt epoxide (1,1-dicarbo substituted oxirane) usually is of the formula II'

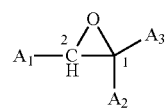

(II')

wherein $A_1$ is hydrogen or an organic carbon anchor group, and $A_2$ and $A_3$ denote the 1,1-dicarbo substituents, each of which, and the organic carbon anchor group $A_1$, if present, are selected from any organic group able to form a carbon-carbon single bond to the carbon atom No. 1 of the oxirane ring, or carbon atom No. 2 in case of $A_1$. Each of $A_1$, $A_2$, $A_3$ may contain one or more further structures of the type 1,1-dicarbo substituted 2-hydro-ethylene oxide which are converted in the reaction. In a preferred process, $A_1$ in formula II' or the below formula II is a carbon anchor group, especially an aryl group, which may carry one or more further structures

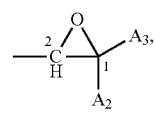

or $A_1$ itself is this structure, to be converted in the present process, while no such structures are present in $A_2$ and $A_3$; or is of the formula II described above. Preferences for residues and educts are as described for the 1-step process (v) described above.

The alpha-hydroxy ketone or alpha-amino ketone formed is preferably a compound of the formula I'

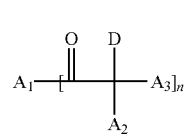

(I')

wherein n ranges from 1 to 4;

D is OH or $NR_{18}R_{19}$;

and $A_1$, $A_2$, $A_3$ and $R_{18}$ and $R_{19}$ are as defined above. Especially preferred $R_{18}$ and $R_{19}$ are methyl. Preferred is an alpha-hydroxykertone product (where D is OH; identical with formula I above).

In step (iii), the reaction is preferably carried out in presence of an aqueous solvent, preferably water or mixtures of water with an organic solvent such as aliphatic or aromatic hydrocarbon, alcohol, ether. Addition of an organic solvent immiscible with water, e.g. hexane, heptane, octane, liquid hydrocarbon fractions like ligroin or petrol ether, benzene, toluene xylene and the like, added before addition of the acid, during the reaction step (iii) or after its completion, may be advantageous for separating the dialcohol product of this step dissolved in the organic phase. The dialcohol product may be isolated, or the whole reaction mixture, preferably the separated organic phase, may be used for the subsequent step (iv).

The acid preferably is a protic acid, advantageously selected from hydrogen halogenides, sulfonic acids, sulfuric acid, acidic hydrogen sulfates, phosphoric acid, carboxylic acids, acidic minerals etc. in water; examples are hydrogen chloride, hydrogen bromide, sulfuric acid, acetic acid, benzoic acid, toluene sulfonic acid, citric acid. Preferably the acid is added to the solution or dispersion of the educt. The amount of acid added preferably ranges from 1 to 20 mol protic hydrogen on 100 mol epoxide.

Temperature often ranges from room temperature to reflux, preferably from 40-100° C.

The oxidizing agent hypochlorite, hypobromite includes, for example, alkaline or alkaline earth or zinc hypochlorites and hypobromites such as LiOCl, NaOCl, KOCl, $Ca(OCl)_2$, LiOBr, NaOBr, KOBr, $Ca(OBr)_2$, $Zn(OCl)_2$, $Zn(OBr)_2$. Most common hypervalent iodine reagents include IBX (1-hydroxy-1,2-benziodoxol-3[1H]-one 1-oxide:

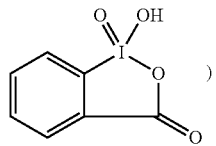

and related iodinanes as described, inter alia, by M. Mülbaier, A. Giannis, ARKIVOC 2003 (vi), 228-236, and publications cited therein.

The oxidizing agent is preferably used in equivalent amounts, relative to the dialcohol to be oxidized, or in excess; examples are 1-20 equivalents of the oxidant per equivalent dialcohol.

The oxidation is preferably carried out in presence of an inert organic solvent such as aliphatic or aromatic hydrocarbons as listed above for step (iii), or ethers, esters, sulfoxides like dimethylsulfoxide (DMSO).

Further components preferably added include water, catalysts, salts and/or pH stabilizing agents. Examples for catalysts include 2,2,6,6-tetramethylpiperidine-1-oxyl (TEMPO), these components are preferably used in amounts ranging from about 0.1 to 10 mol-% relative to the dialcohol. Further components include alkaline halogenides, hydrogencarbonates like sodium chloride or bromide, sodium hydrogen carbonate, potassium chloride or bromide, potassium hydrogen carbonate.

Catalysts as well as oxidizing agents may be used as such or in immobilized or modified form (e.g. resin-bonded TEMPO or IBX).

The temperature during the oxidation step is preferably kept within the range from −15° C. to about room temperature, preferably from −10 to +15° C.

After completing the oxidation, any aqueous phase, if present, is preferably separated. Remaining excess oxidant may be neutralized using a suitable reducing agent (e.g. sodium dithionite).

General Conditions

As protecting groups Pr, the usual moieties known in the art for the protection of hydroxy functions may be employed. Alcohol protecting moieties include, but are not limited to, hydroxyl protecting groups known in the art (see, for example, Greene, T. W. Protective Groups in Organic Synthesis (Wiley, New York, 1981)). The term includes moieties which can be removed and/or derivatized after the formation of the ketone in accordance with the methods of the invention to yield the free alcohol. Advantageously, the alcohol protecting moiety is inert to the conditions used to generate the ketone. Examples are carbonates such as the benzoxycarbonyl or butyloxycarbonyl (BOC) group, or suitable sulphonyl or acyl residues such as p-toluenesulphonyl (tosyl), phthalyl or trifluoroacetyl, methoxymethyl ethers (MOM), beta-methoxyethoxymethyl ethers (MEM), tetrahydropyranyl ethers (THP), methylthiomethyl ethers (MTM), benzyl groups, and silyl ethers (e.g., trimethyl silyl ethers (TMS), t-butyldimethyl silyl ethers (TBDMS)). Methods of introducing or removing these groups are well known in the art and described, inter alia, in textbooks of organic chemistry or review articles. Furthermore, the term "alcohol protecting moiety" may include alkyl, alkenyl, alkynyl, aralkyl, aryl, and heteroaryl moieties.

Before carrying out the present process steps iii-v, especially primary and secondary alcohol groups within the epoxy educt are advantageously transferred into the group OPr where Pr is the protecting group. Once the desired hydroxyketone or aminoketone has been formed, the alcohol functions may conveniently be recovered by removing the group Pr according to conventional methods. Thus, present invention also pertains to a process wherein v) a 1,1-dicarbo substituted 2-hydro-ethylene oxide, e.g. a compound of the above formula II or II', containing a substituent OPr, wherein Pr is a protecting group, especially a substituent OPr in $CH_2$—OPr or CH—OPr, is objected to aerobic oxidation in the presence of a transition metal catalyst as explained above, and vi) the protecting group is subsequently removed, thus recovering the OH functionality.

Number indices in residue symbols such as $A_1$, $A_2$, $A_3$, $R_1$, $R_2$, $R_3$, $R_4$ etc. denote the type of residue and not the number of residues attached; in case that more than one residue of this type is attached, the symbol is in brackets and number is indicated by a further number index outside the brackets, for example: $(R_1)_2$ denotes 2 residues of the type $R_1$, $(R_1)_3$ denotes 3 residues of the type $R_1$, $(R_2)_2$ denotes 2 residues of the type $R_2$, $(R_2)_3$ denotes 3 residues of the type $R_2$.

In more preferred processes, educts, intermediates and products, $A_1$, if n is 1, is phenyl which is unsubstituted or substituted by OPr, $NR_9R_{10}$, carboxy, $COR_1$, $SO_2R_2$, halogen, nitro, CN, Aro; and/or by $C_1$-$C_{18}$alkyl, $C_1$-$C_{18}$alkoxy, $C_2$-$C_{18}$alkenyl or $C_2$-$C_{18}$alkenyloxy, each of which itself is unsubstituted or substituted by OPr, halogen, $NR_9R_{10}$, carboxy, Aro, $COR_1$, $SO_2R_2$, nitro, CN; or is phenyl substituted by O—$R_8$—O—$SiR_{11}R_{12}R_{13}$; or $A_1$ is $C_1$-$C_{18}$alkyl, $C_1$-$C_{18}$alkoxy, $C_2$-$C_{18}$alkenyl or $C_2$-$C_{18}$alkenyloxy, each of which is unsubstituted or substituted by OPr, halogen, $NR_9R_{10}$, Aro, $COR_1$, $OCOR_3$, $NR_9COR_3$, and/or, if containing at least 3 carbon atoms, can be interrupted in a carbon-carbon single bond by O, $NR_9$, COO, $CONR_9$;

$A_1$, if n is 2, is Ar—$R_5$—Ar; or is a residue $R_{11}R_{12}Si(O$—$R_8$—O—$Ar)_2$;

$A_1$, if n is 3, is a residue $(Ar)_3$—$R_6$; or is a residue $R_{11}Si(O$—$R_8$—O—$Ar)_3$;

$A_1$, if n is 4, is a residue $(Ar)_4$—$R_7$;

$A_2$ and $A_3$ independently are $C_1$-$C_{18}$alkyl; $C_2$-$C_{18}$alkenyl; $C_4$-$C_{12}$cycloalkyl; $C_5$-$C_{12}$cycloalkenyl; phenyl; $C_7$-$C_{15}$-phenylalkyl; $C_7$-$C_{15}$cyclohexylalkyl; or one of said residues substituted by OPr, $NR_9R_{10}$, COOH, $COR_1$, $SO_2R_2$, halogen, nitro, CN; and/or, if containing at least 3 carbon atoms, are interrupted in a carbon-carbon single bond by O, $NR_9$, COO, $OCONR_9$, $CONR_9$; or $A_2$ and $A_3$ together are $C_4$-$C_{11}$alkylene, -oxaalkylene, -azaalkylene or -alkenylene, each of which is unsubstituted or substituted by OPr, $NR_9R_{10}$, carboxy, $COR_1$, $SO_2R_2$, halogen, nitro, CN, and/or by a residue selected from $C_1$-$C_{18}$alkyl, $C_1$-$C_{18}$alkoxy, $C_2$-$C_{18}$alkenyl, $C_2$-$C_{18}$alkenyloxy, each of which itself is unsubstituted or substituted by OPr, amino, carboxy, $COR_1$, $SO_2R_2$, halogen, nitro, CN;

where further meanings are as defined for formulae I and II below;
and especially $A_1$, if n is 1, is phenyl which is unsubstituted or substituted by $C_1$-$C_{12}$alkyl, $C_1$-$C_{12}$alkoxy, $C_1$-$C_{12}$alkyl substituted by OPr, $C_2$-$C_{12}$alkoxy substituted by OPr; or is phenyl substituted by O—$R_8$—O—Si—$(CH_3)_3$;

$A_1$, if n is 2, is a residue phenylene-$R_5$-phenylene; or is a residue $(CH_3)_2Si(O$—$R_8$—O-phenylene$)_2$;

$A_1$, if n is 3, is a residue (phenylene)$_3$-$R_6$; or is a residue $CH_3Si(O$—$R_8$—O-phenylene$)_3$;

$A_1$, if n is 4, is a residue (phenylene)$_4$-$R_7$;

$A_2$ and $A_3$ independently are $C_1$-$C_4$alkyl, or together are pentamethylene.

Any aryl usually is $C_4$-$C_{12}$aryl, especially carbocyclic aryl such as $C_6$-$C_{10}$aryl including phenyl and naphthyl. Aryl means mostly $C_6$-$C_{12}$aryl, preferably phenyl or naphthyl, especially phenyl. Aralkyl is usually the alkyl as defined below, which is substituted by the above aryl; preferred is $C_7$-$C_{11}$-phenylalkyl. Alk(yl)aryl is the above aryl substituted by alkyl; preferred is phenyl mono-, di- or trisubstituted by $C_1$-$C_4$alkyl. Ar may be derived from these aryl groups by abstraction of a hydrogen atom from aryl carbon; most preferred Ar is phenylene. Ar moieties may also be interconnected by a tri- or tetravalent spacer $R_5$; in this case, Ar also embraces trivalent aryl, which may be derived from one of the above aryl groups by abstraction of 2 hydrogen atoms from aryl carbon.

Groups which may be unsubstituted or substituted by selected radicals such as $C_6$-$C_{12}$aryl or $C_5$-$C_{12}$cycloalkyl, like a phenyl or a cyclohexyl ring, are preferably unsubstituted or mono-, di- or tri-substituted, especially preferred are these groups unsubstituted or mono- or disubstituted.

Halogen usually stands for fluoro, chloro, bromo, iodo; preferred is chloro and bromo, especially chloro.

Alkyl usually is $C_1$-$C_{18}$alkyl embracing branched and unbranched alkyl, for example, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5, 5-hexamethylhexyl, tridecyl, tetradecyl, pentadecyl, hexadecyl, heptadecyl, octadecyl.

Alkoxy stands for alkyl linked over an oxygen atom as spacer: —O-alkyl.

Alkenyl includes, within the scope of the definitions given, inter alia vinyl, allyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl and n-octadec-4-enyl.

Alkenyloxy stands for alkenyl linked over an oxygen atom as spacer: —O-alkenyl; it often embraces $C_3$-$C_{12}$alkenyloxy.

Alkyl interrupted by —O—, —NH—, —$NR_9$— and/or by —S— may be interrupted by one or more of the mentioned groups, in each case normally one group being inserted into a bond and hetero-hetero bonds, such as, for example, O—O, S—S, NH—NH etc. not occurring; if the interrupted alkyl is, in addition, substituted, the substituents are not normally in the α-position with respect to the hetero atom. If a plurality of interrupting groups of the type —O—, —NH—, —$NR_9$— and —S— occurs in a radical, those groups are usually identical.

$C_4$-$C_{11}$alkylene stands for a divalent $C_4$-$C_{11}$alkyl group wherein the second valency is obtained by abstraction of a hydrogen atom; the term includes "alkylidene". Oxaalkylene, azaalkylene are alkylene interrupted by oxygen or $NR_9$, as explained above.

Alkenylene includes, within the scope of the definitions given, $C_2$-$C_{12}$alkylene; the term stands for a divalent alkylene group wherein the second valency is obtained by abstraction of a hydrogen atom; the term includes "alkenylidene".

A divalent carbocyclic aryl often is phenylene.

Aryloxy stands for aryl linked over an oxygen atom as spacer: —O-aryl, e.g. phenoxy.

Cycloalkyl mainly embraces $C_5$-$C_{12}$cycloalkyl including cyclopentyl, cyclohexyl, cycloheptyl, cyclooctyl, cyclononyl, cyclodecyl, cycloundecyl and cyclodocecyl. Cyclopentyl, cyclohexyl, cyclooctyl and cyclododecyl are preferred.

Cycloalkenyl mainly embraces $C_5$-$C_{12}$cycloalkenyl including cyclopentenyl, cyclohexenyl, cycloheptenyl, cyclooctenyl, cyclononenyl, cyclodecenyl, cycloundecenyl and cyclodocecenyl. Cyclohexenyl is preferred.

Cycloalkoxy stands for cycloalkyl linked over an oxygen atom as spacer: —O-cycloalkyl, e.g. cyclohexyloxy.

Cycloalkenoxy stands for cycloalkenyl linked over an oxygen atom as spacer: —O-cycloalkenyl, e.g. cyclohexenyloxy.

$R_5$ is a divalent spacer group covalently bonding the Ar moieties attached; it includes a direct bond; a heteroatomic spacer selected from —O—, —$NR_9$—, —S—, —SO—, $SO_2$—, CO, COO; $C_1$-$C_{18}$alkylene; $C_3$-$C_{18}$alkenylene; or $C_1$-$C_{18}$-alkylene interrupted or end-capped by —O—, —$NR_9$—, —S—, —SO—, $SO_2$—, CO, COO, $CONR_9$, $OCONR_9$, OCOO and/or substituted by OPr or $NR_9R_{10}$. Other suitable linkers are 1,3-cyclohexanediyl, 1,4-cyclohexanediyl, 4-methyl-1,3-cyclohexanediyl or are selected from the following structures:

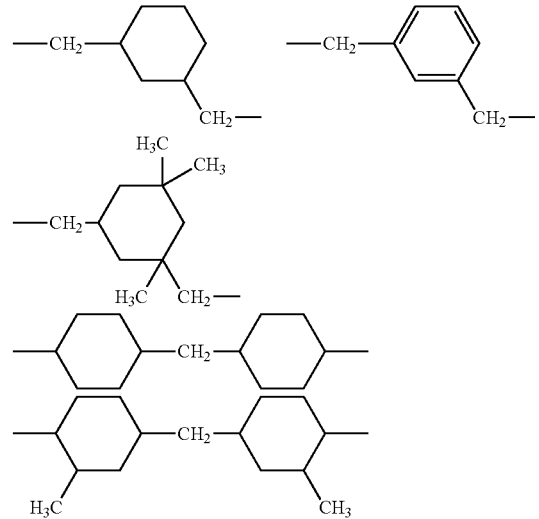

or $R_5$ is a tri- or tetravalent $C_3$-$C_{12}$alkyl moiety with 2 of its chemical bonds attached to one Ar and its $3^{rd}$ and, if present, $4^{th}$ chemical bond attached to the other Ar moiety.

$R_6$ is a trivalent spacer group covalently bonding the Ar moieties attached; it includes $C_2$-$C_{18}$-alkane-triyl optionally interrupted or end-capped by —O—, —$NR_9$—, —S—, —SO—, $SO_2$—, CO, COO, $CONR_9$, $OCONR_9$, OCOO, and/ or cyclohexylene or phenylene structures, e.g. as listed above for $R_5$, and which is unsubstituted or substituted by OPr or $NR_9R_{10}$; or $C_3$-$C_{18}$alkene-triyl.

$R_7$ is a tetravalent spacer group covalently bonding the Ar moieties attached; it includes $C_2$-$C_{18}$-alkane-tetryl optionally interrupted or end-capped by —O—, —NR$_9$—, —S—, —SO—, SO$_2$—, CO, COO, CONR$_9$, OCONR$_9$, OCOO, and/or cyclohexylene or phenylene structures, e.g. as listed above for $R_5$, and which is unsubstituted or substituted by OPr or NR$_9$R$_{10}$; or $C_4$-$C_{18}$alkene-tetryl.

$R_8$ as a divalent aliphatic or cycloaliphatic residue includes $C_1$-$C_{18}$alkylene; or $C_3$-$C_{38}$-alkylene interrupted by —O—, —NR$_9$—, —S—, —SO—, SO$_2$—, CO, COO, CONR$_9$, OCONR$_9$, OCOO. Other suitable linkers are 1,3-cyclohexanediyl, 1,4-cyclohexanediyl, 4-methyl-1,3-cyclohexanediyl or are selected from the following structures:

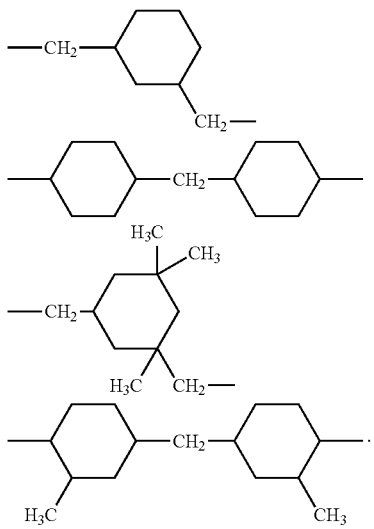

In a preferred process, compounds of formulae I and II are those wherein $A_1$, if n is 1, is phenyl which is unsubstituted or substituted by OPr, NR$_9$R$_{10}$, carboxy, COR$_1$, SO$_2$R$_2$, halogen, nitro, CN, Aro; and/or by $C_1$-$C_{18}$alkyl, $C_1$-$C_{18}$alkoxy, $C_2$-$C_{18}$alkenyl or $C_2$-$C_{18}$alkenyloxy, each of which itself is unsubstituted or substituted by OPr, halogen, NR$_9$R$_{10}$, carboxy, Aro, COR$_1$, SO$_2$R$_2$, nitro, CN; or is phenyl substituted by O—R$_8$—O— SiR$_{11}$R$_{12}$R$_{13}$; or $A_1$ is $C_1$-$C_{18}$alkyl, $C_1$-$C_{18}$alkoxy, $C_2$-$C_{18}$alkenyl or $C_2$-$C_{18}$alkenyloxy, each of which is unsubstituted or substituted by OPr, halogen, NR$_9$R$_{10}$, Aro, COR$_1$, OCOR$_3$, NR$_9$COR$_3$, and/or, if containing at least 3 carbon atoms, can be interrupted in a carbon-carbon single bond by O, NR$_9$, COO, CONR$_9$;

$A_1$, if n is 2, is Ar—R$_5$—Ar; or is a residue R$_{11}$R$_{12}$Si(O—R$_8$—O—Ar)$_2$; $A_1$, if n is 3, is a residue (Ar)$_3$—R$_6$; or is a residue R$_{11}$Si(O—R$_8$—O—Ar)$_3$;

$A_1$, if n is 4, is a residue (Ar)$_4$—R$_7$;

$A_2$ and $A_3$ independently are $C_1$-$C_{18}$alkyl; $C_2$-$C_{18}$alkenyl; $C_4$-$C_{12}$cycloalkyl; $C_5$-$C_{12}$cycloalkenyl; phenyl; $C_7$-$C_{15}$-phenylalkyl; $C_7$-$C_{15}$cyclohexylalkyl; or one of said residues substituted by OPr, NR$_9$R$_{10}$, COOH, COR$_1$, SO$_2$R$_2$, halogen, nitro, CN; and/or, if containing at least 3 carbon atoms, are interrupted in a carbon-carbon single bond by O, NR$_9$, COO, OCONR$_9$, CONR$_9$;

or $A_2$ and $A_3$ together are $C_4$-$C_{11}$alkylene, -oxaalkylene, -azaalkylene or -alkenylene, each of which is unsubstituted or substituted by OPr, NR$_9$R$_{10}$, carboxy, COR$_1$, SO$_2$R$_2$, halogen, nitro, CN, and/or by a residue selected from $C_1$-$C_{18}$alkyl, $C_1$-$C_{18}$alkoxy, $C_2$-$C_{18}$alkenyl, $C_2$-$C_{18}$alkenyloxy, each of which itself is unsubstituted or substituted by OPr, amino, carboxy, COR$_1$, SO$_2$R$_2$, halogen, nitro, CN;

Ar is phenylene, which is unsubstituted or substituted by OPr, NR$_9$R$_{10}$, carboxy, COR$_1$, SO$_2$R$_2$, halogen, nitro, CN, $C_1$-$C_{18}$alkyl, $C_1$-$C_{18}$alkoxy, $C_2$-$C_{18}$alkenyl, $C_2$-$C_{18}$alkenyloxy, phenoxy;

$R_1$ is hydrogen, OH, $C_1$-$C_{18}$alkyl; $C_2$-$C_{18}$alkenyl; $C_4$-$C_{12}$cycloalkyl; $C_5$-$C_{12}$cycloalkenyl; phenyl, $C_7$-$C_{18}$alkylphenyl, $C_1$-$C_{18}$alkoxyphenyl, $C_1$-$C_{18}$alkoxy, $C_2$-$C_{18}$alkenoxy, $C_4$-$C_{12}$cycloalkoxy, $C_5$-$C_{12}$cycloalkenoxy, phenoxy, $C_7$-$C_{18}$alkylphenoxy, $C_7$-$C_{18}$alkoxyphenoxy;

$R_2$ is OH, $C_1$-$C_{18}$alkyl or $C_1$-$C_{18}$alkoxy;

$R_3$ is $C_1$-$C_{18}$alkyl; $C_2$-$C_{18}$alkenyl; $C_4$-$C_{12}$cycloalkyl; $C_5$-$C_{12}$cycloalkenyl;

phenyl, $C_7$-$C_{18}$alkylphenyl, $C_1$-$C_{18}$alkoxyphenyl;

$R_5$ is a direct bond; a heteroatomic spacer selected from —O—, —NR$_9$—, —S—, —SO—, SO$_2$—, CO, COO; $C_1$-$C_{18}$alkylene; $C_3$-$C_{18}$alkenylene; or $C_1$-$C_{18}$-alkylene interrupted or end-capped by —O—, —NR$_9$—, —S—, —SO—, SO$_2$—, CO, COO, CONR$_9$, OCONR$_9$, OCOO, cyclohexylene, phenylene and/or substituted by OPr or NR$_9$R$_{10}$; or $R_5$ is a tri- or tetravalent $C_3$-$C_{12}$alkyl moiety with 2 of its chemical bonds attached to one Ar and its $3^{rd}$ and, if present, $4^{th}$ chemical bond attached to the other Ar moiety;

$R_6$ is $C_2$-$C_{18}$-alkane-triyl optionally interrupted or end-capped by —O—, —NR$_9$—, —S—, —SO—, SO$_2$—, CO, COO, CONR$_9$, OCONR$_9$, OCOO, cyclohexylene, phenylene, and which is unsubstituted or substituted by OPr or NR$_9$R$_{10}$; or is $C_3$-$C_{18}$alkene-triyl;

$R_7$ is $C_2$-$C_{18}$-alkane-tetryl optionally interrupted or end-capped by —O—, —NR$_9$—, —S—, —SO—, SO$_2$—, CO, COO, CONR$_9$, OCONR$_9$, OCOO, cyclohexylene, phenylene, and which is unsubstituted or substituted by OPr or NR$_9$R$_{10}$; or is $C_4$-$C_{18}$alkene-tetryl;

$R_8$ is $C_1$-$C_{18}$-alkylene, or $C_3$-$C_{36}$alkylene interrupted by —O—, —NR$_9$—, —S—, —SO—, SO$_2$—, CO, COO, CONR$_9$, OCONR$_9$, OCOO, cyclohexylene;

$R_9$ and $R_{10}$ independently are hydrogen, $C_1$-$C_{12}$alkyl, $C_1$-$C_{12}$alkyl substituted by OPr, cyclohexyl;

or $R_9$ and $R_{10}$ are joined together to form a pentamethylene or oxapentamethylene moiety;

$R_{11}$, $R_{12}$ and $R_{13}$ independently are $C_1$-$C_{12}$alkyl or $C_1$-$C_{12}$alkoxy;

especially wherein $A_1$, if n is 1, is phenyl which is unsubstituted or substituted by $C_1$-$C_{12}$alkyl, $C_1$-$C_{12}$alkoxy, $C_1$-$C_{12}$alkyl substituted by OPr, $C_2$-$C_{12}$alkoxy substituted by OPr; or is phenyl substituted by O—R$_8$—O—Si—(CH$_3$)$_3$;

$A_1$, if n is 2, is a residue phenylene-R$_5$-phenylene; or is a residue (CH$_3$)$_2$Si(O—R$_8$—O-phenylene)$_2$;

$A_1$, if n is 3, is a residue (phenylene)$_3$-R$_6$; or is a residue CH$_3$Si(O—R$_8$—O-phenylene)$_3$;

$A_1$, if n is 4, is a residue (phenylene)$_4$-R$_7$;

$A_2$ and $A_3$ independently are $C_1$-$C_4$alkyl, or together are pentamethylene;

$R_5$ is a direct bond; —O—; —NR$_9$—; CO; $C_1$-$C_{12}$alkylene; $C_1$-$C_4$-alkylene substituted by OPr or NR$_9$R$_{10}$; $C_2$-$C_4$alkylene interrupted by —O—, —NR$_9$—; or $R_5$ is a trivalent $C_3$-$C_{12}$alkyl moiety with 2 of its chemical bonds attached to one phenylene and its $3^{rd}$ chemical bond attached to the other phenylene moiety;

$R_6$ is $C_3$-$C_{18}$-alkane-triyl; or $C_3$-$C_{18}$alkane-triyl interrupted —O—, —NR$_9$—, COO, CONR$_9$, OCONR$_9$, OCOO; or is $C_3$-$C_{18}$alkene-triyl;

$R_7$ is $C_4$-$C_{18}$-alkane-tetryl; or $C_4$-$C_{18}$alkane-tetryl interrupted by —O—, —NR$_9$—, COO, CONR$_9$, OCONR$_9$, OCOO, phenylene, cyclohexylene; or is $C_4$-$C_{18}$alkene-tetryl;

$R_8$ is $C_2$-$C_{18}$-alkylene, or $C_3$-$C_{36}$alkylene interrupted by —O—, —NR$_9$—, COO, CONR$_9$, OCONR$_9$, OCOO, cyclohexylene;

$R_9$ and $R_{10}$ independently are hydrogen, $C_1$-$C_{12}$alkyl; or together are oxapentamethylene;

$R_{11}$, $R_{12}$ and $R_{13}$ independently are $C_1$-$C_4$alkyl;

each as long as within the specific definitions given for each process step above.

In preferred process steps for the preparation of a hydroxyketone or aminoketone, the epoxide educt used is the one obtained in steps i) and ii) initially described.

Throughout the process steps described, pressure is not critical, the reactions may be carried out, for example, under normal pressure or elevated pressures usual in chemical synthesis, e.g. 0.5-150 bar. Elevated pressures may be advantageous in case that more volatile substances (e.g. dimethyl sulphide, methyl chloride etc. as educt in step i) are employed.

Workup and, if desired, isolation and/or purification of any intermediate or the α-hydroxyketone product may be effected following methods known in the art such as extraction of aqueous phase with organic solvent, drying, crystallization and/or recrystallization (effected, for example, by removing the solvent, cooling, seeding etc.), distillation, chromatography etc.; the procedures given in the examples for these operation may be generalized or replaced by other suitable means of general use in synthetic organic chemistry in laboratory or industrial scale.

Novel Epoxides

Some of the epoxide intermediates used in present invention are novel compounds. Compounds of the formula III

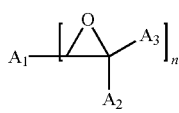

(III)

wherein
n ranges from 2 to 4, $A_1$, if n is 2, is Ar—$R_5$—Ar; or is a residue $R_{11}R_{12}$Si(O—$R_8$—O—Ar)$_2$; or $A_1$ is a direct bond;

$A_1$, if n is 3, is a residue (Ar)$_3$—$R_6$; or is a residue $R_{11}$Si(O—$R_8$—O—Ar)$_3$;

$A_1$, if n is 4, is a residue (Ar)$_4$—$R_7$;

$A_2$ and $A_3$ independently are $C_1$-$C_{18}$alkyl; $C_2$-$C_{18}$alkenyl; $C_4$-$C_{12}$cycloalkyl; $C_5$-$C_{12}$cycloalkenyl;

phenyl; $C_7$-$C_{15}$-phenylalkyl; $C_7$-$C_{15}$cyclohexylalkyl; or one of said residues substituted by OPr, NR$_9$R$_{10}$, COOH, COR$_1$, SO$_2$R$_2$, halogen, nitro, CN; and/or, if containing at least 3 carbon atoms, are interrupted in a carbon-carbon single bond by O, NR$_9$, COO, OCONR$_9$, CONR$_9$;

or $A_2$ and $A_3$ together are $C_4$-$C_{11}$alkylene, -oxaalkylene, -azaalkylene or -alkenylene, each of which is unsubstituted or substituted by OPr, NR$_9$R$_{10}$, carboxy, COR$_1$, SO$_2$R$_2$, halogen, nitro, CN, and/or by a residue selected from $C_1$-$C_{18}$alkyl, $C_1$-$C_{18}$alkoxy, $C_2$-$C_{18}$alkenyl, $C_2$-$C_{18}$alkenyloxy, each of which itself is unsubstituted or substituted by OPr, amino, carboxy, COR$_1$, SO$_2$R$_2$, halogen, nitro, CN;

Ar is phenylene, which is unsubstituted or substituted by OPr, NR$_9$R$_{10}$, carboxy, COR$_1$, SO$_2$R$_2$, halogen, nitro, CN, $C_1$-$C_{18}$alkyl, $C_1$-$C_{18}$alkoxy, $C_2$-$C_{18}$alkenyl, $C_2$-$C_{18}$alkenyloxy, phenoxy;

$R_1$ is hydrogen, OH, $C_1$-$C_{18}$alkyl; $C_2$-$C_{18}$alkenyl; $C_4$-$C_{12}$cycloalkyl; $C_5$-$C_{12}$cycloalkenyl;

phenyl, $C_7$-$C_{18}$alkylphenyl, $C_1$-$C_{18}$alkoxyphenyl, $C_1$-$C_{18}$alkoxy, $C_2$-$C_{18}$alkenoxy, $C_4$-$C_{12}$cycloalkoxy, $C_5$-$C_{12}$cycloalkenoxy, phenoxy, $C_7$-$C_{18}$alkylphenoxy, $C_7$-$C_{18}$alkoxyphenoxy;

$R_2$ is OH, $C_1$-$C_{18}$alkyl or $C_1$-$C_{18}$alkoxy;

$R_3$ is $C_1$-$C_{18}$alkyl; $C_2$-$C_{18}$alkenyl; $C_4$-$C_{12}$cycloalkyl; $C_5$-$C_{12}$cycloalkenyl;

phenyl, $C_7$-$C_{18}$alkylphenyl, $C_1$-$C_{18}$alkoxyphenyl;

$R_5$ is a direct bond; a heteroatomic spacer selected from —O—, —NR$_9$—, —S—, —SO—, SO$_2$—, CO, COO; $C_1$-$C_{18}$alkylene; $C_3$-$C_{18}$alkenylene; or $C_1$-$C_{18}$-alkylene interrupted or end-capped by —O—, —NR$_9$—, —S—, —SO—, SO$_2$—, CO, COO, CONR$_9$, OCONR$_9$, OCOO, cyclohexylene, phenylene and/or substituted by OPr or NR$_9$R$_{10}$; or $R_5$ is a tri- or tetravalent $C_3$-$C_{12}$alkyl moiety with 2 of its chemical bonds attached to one Ar and its 3$^{rd}$ and, if present, 4$^{th}$ chemical bond attached to the other Ar moiety;

$R_6$ is $C_2$-$C_{18}$-alkane-triyl optionally interrupted or end-capped by —O—, —NR$_9$—, —S—, —SO—, SO$_2$—, CO, COO, CONR$_9$, OCONR$_9$, OCOO, cyclohexylene, phenylene, and which is unsubstituted or substituted by OPr or NR$_9$R$_{10}$; or is $C_3$-$C_{18}$alkene-triyl;

$R_7$ is $C_2$-$C_{18}$-alkane-tetryl optionally interrupted or end-capped by —O—, —NR$_9$—, —S—, —SO—, SO$_2$—, CO, COO, CONR$_9$, OCONR$_9$, OCOO, cyclohexylene, phenylene, and which is unsubstituted or substituted by OPr or NR$_9$R$_{10}$; or is $C_4$-$C_{18}$alkene-tetryl;

$R_8$ is $C_1$-$C_{18}$-alkylene, or $C_3$-$C_{36}$alkylene interrupted by —O—, —NR$_9$—, —S—, —SO—, SO$_2$—, CO, COO, CONR$_9$, OCONR$_9$, OCOO, cyclohexylene;

$R_9$ and $R_{10}$ independently are hydrogen, $C_1$-$C_{12}$alkyl, $C_1$-$C_{12}$alkyl substituted by OPr, cyclohexyl;

or $R_9$ and $R_{10}$ are joined together to form a pentamethylene or oxapentamethylene moiety;

$R_{11}$, $R_{12}$ and $R_{13}$ independently are $C_1$-$C_{12}$alkyl or $C_1$-$C_{12}$alkoxy;

and more preferred meanings or any other residue are as defined above for formulae I and II, therefore are another object of the invention.

Examples for compounds obtainable according to the invention include the following:

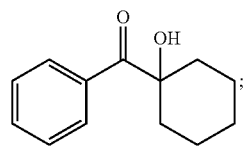
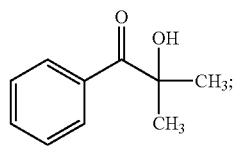
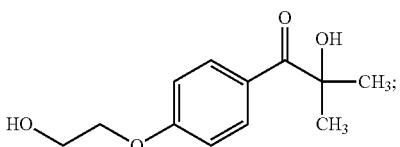

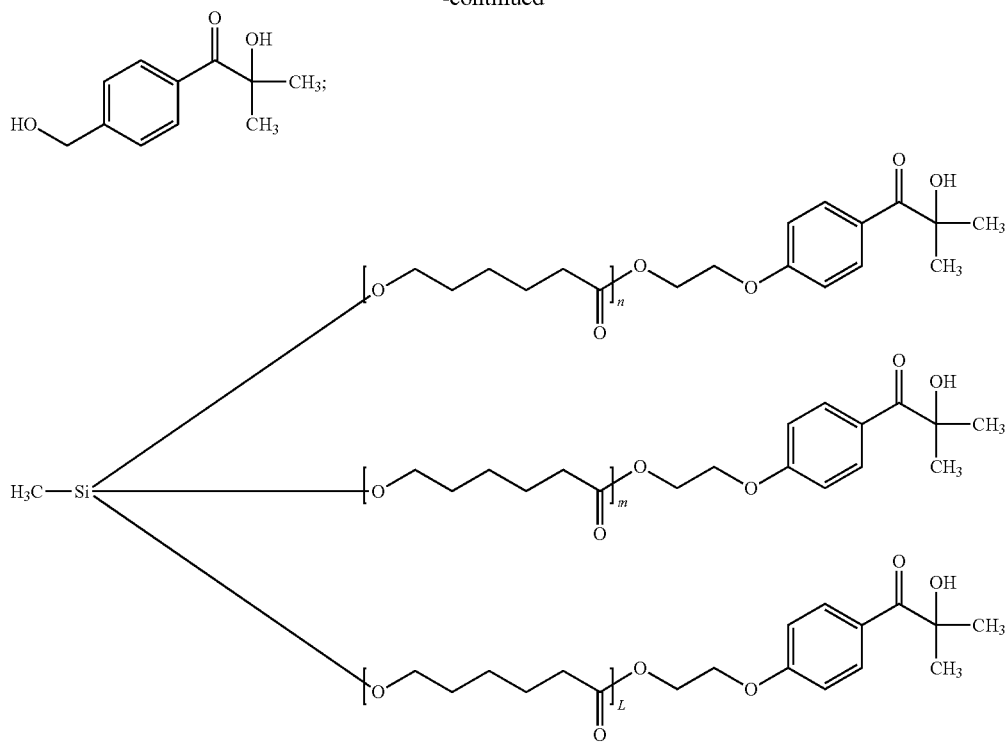
where L, m and n have an average value of about 3;
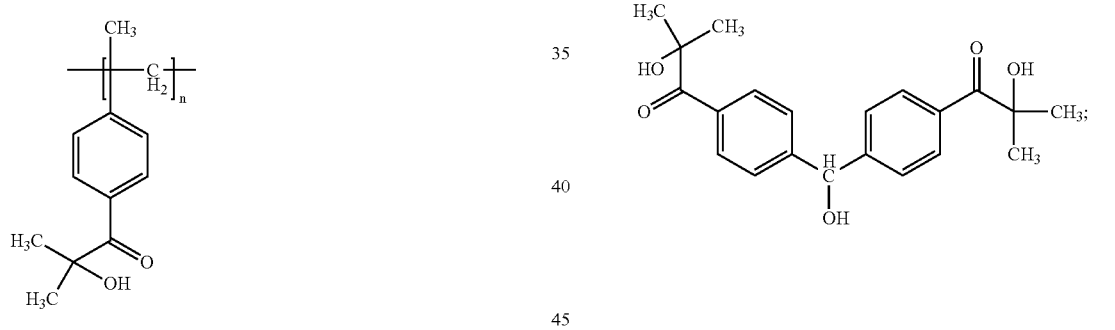
where p may range, for example, from 2 to 10, such as in compounds of CAS Nos. 163702-01-0; 75980-60-8; 954-16-5; 134-84-9;
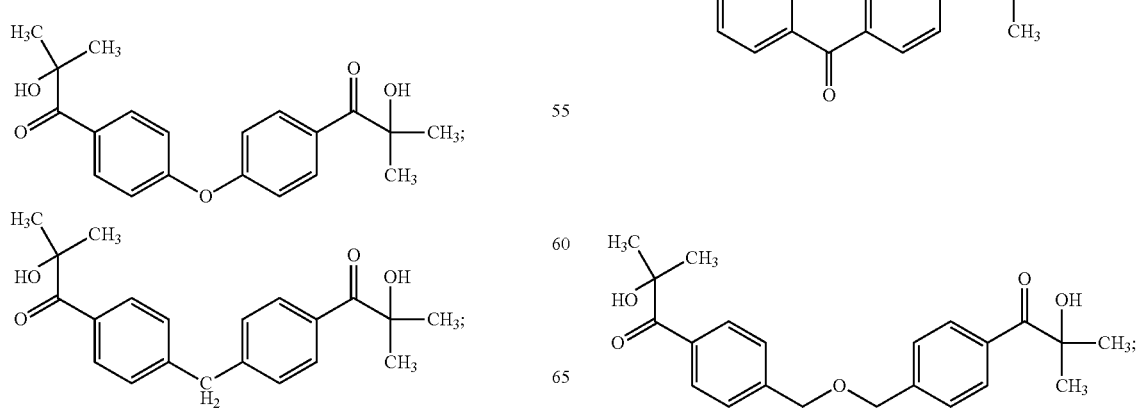

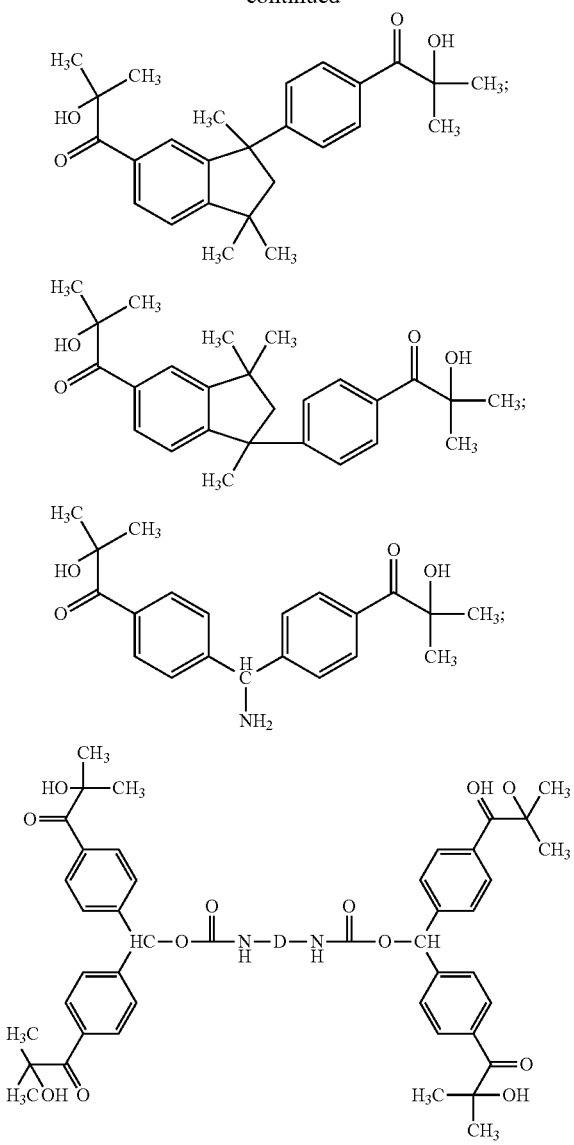

where D is $C_2$-$C_{12}$alkylene, phenylene or cyclohexylene;

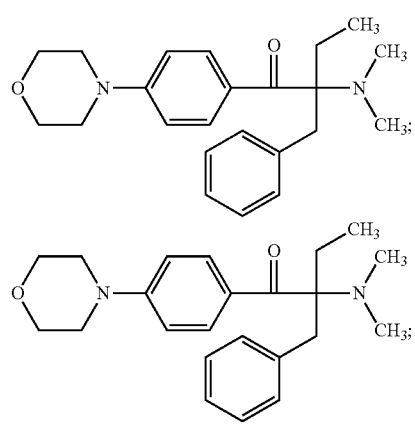

as well as mixtures thereof.

Compounds obtained in the process of present invention can subsequently be further modified following methods known in the art.

Many of the compounds obtainable according to the invention, such as the compounds of the formula I, can be used as photoinitiators for photopolymerization of ethylenically unsaturated compounds or mixtures containing such compounds. Thus, the process of present invention provides a new approach for the preparation of photoinitiators of the alpha-hydroxy ketone and alpha-amino ketone classes.

The α-hydroxy ketone photoinitiators obtainable according to the present invention are, for example, of the formula

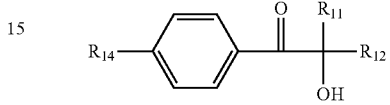

where
$R_{11}$ and $R_{12}$ independently of one another are hydrogen, $C_1$-$C_6$ alkyl, phenyl, $C_1$-$C_6$ alkoxy, $OSiR_{16}(R_{17})_2$ or $-O(CH_2CH_2O)_q-C_1$-$C_6$ alkyl, or
$R_{11}$ and $R_{12}$, together with the carbon atom to which they are attached, form a cyclohexyl ring;
q is a number from 1 to 20;
$R_{14}$ is hydrogen, $C_1$-$C_{18}$ alkyl, $C_1$-$C_{18}$ alkoxy, $-OCH_2CH_2-OR_{15}$, a group $CH_2=C(CH_3)-$ or is

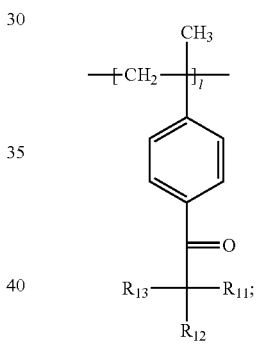

l is a number from 2 to 10;
$R_{15}$ is hydrogen, $-COCH=CH_2$ or $-COC(CH_3)=CH_2$; and
$R_{16}$ and $R_{17}$ independently of one another are $C_1$-$C_8$ alkyl or phenyl.

Compounds of this class are disclosed, for example, in WO03046017, and references cited therein.

Another example of an alpha-hydroxy ketone is a compound of the formula

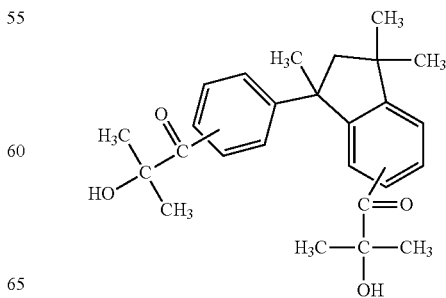

for example ESACURE® KIP from Fratelli Lamberti, 2-hydroxy-1-{1-[4-(2-hydroxy-2-methyl-propionyl)-phenyl]-1,3,3-trimethyl-indan-5-yl}-2-methyl-propan-1-one.

Irgacure® and Darocur® products are available from Ciba Specialty Chemicals Inc.; present α-hydroxy ketone photoinitiator is for example α-hydroxycyclohexylphenyl ketone, available from Ciba Specialty Chemicals as Irgacure® 184.

Abbreviations used in specification and examples:
TEMPO 2,2,6,6-tetramethyl-4-oxo-piperidine
Alox aluminum oxide
Room temperature denotes a temperature in the range 20-25° C.

EXAMPLE 1

Preparation of the Epoxide

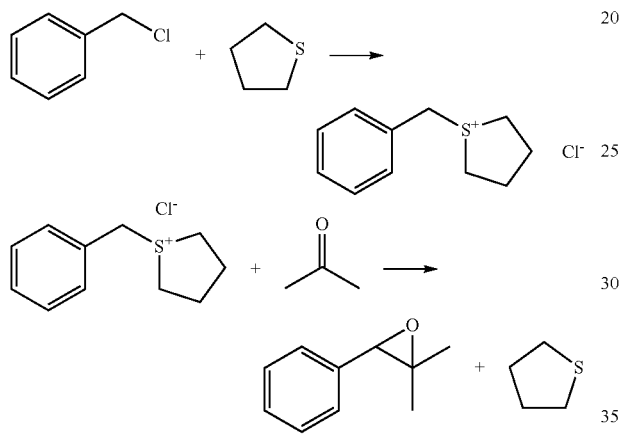

A mixture of 586 g (4.6 mol) benzyl chloride and 418 g (4.6 mol) tetrahydrothiophene in 1 L water is heated to 85° C. with stirring until a clear and homogen, or slightly hazy single phased solution is obtained. This solution is cooled to 20° C. and added dropwise to a reaction mixture consisting of 1104 g of 50% NaOH (13.8 mol) and 935 g of acetone (16.1 mol) in 250 g of methanol. After the addition, the reaction mixture is kept without stirring for 10 min. for phase separation. After separation of the organic phase, the product is isolated by distillation, yielding 750 g of the desired crude product, which is used for the next reaction step without further purification.

EXAMPLE 2 a)

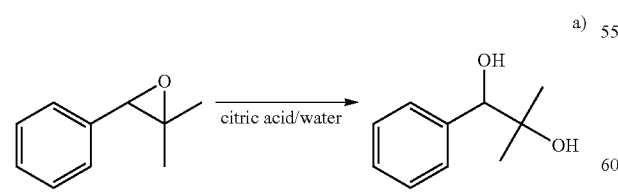

A mixture of 610 g (50-60% b.w. solution in water, 2.3 mol) of the crude epoxide from example 1 and 68 g (0.324 mol) citric acid in 1.7 litres of water is heated to 80° C. and stirred at this temperature until no educt can be found any more by thin layer chromatography (ca. 6 h). 1.5 l of heptane are then added at 80° C., the mixture is stirred for 10 minutes and then allowed to separate for another 10 min. The organic phase is cooled to 0° C. and precipitation is induced by addition of a seeding crystal. 250 g (65%) of the diol are obtained.

b)

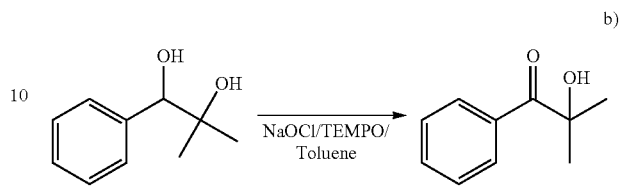

A solution of 3.5 g (29.7 mmol) KBr in 50 ml water is added to a solution of 50 g (0.297 mol) of the diol obtained in part (a) in 300 ml of toluene. Then 0.9 g (5.76 mmol) TEMPO is added. The reddish suspension is cooled to 0° C. 160 ml of a 12% solution of sodium hypochlorite (0.3 mol) is added with maintaining the internal temperature at 5° C. or lower. The mixture is subsequently stirred for 1 h at 0-5° C. and then allowed to separate for 10 min. 400 ml of sodium dithionite solution (obtained from 30 g sodium dithionite (85%) and 400 ml of water) is added to the organic phase and stirred at 85° C. for 1-2 h. The organic phase is again separated and concentrated (rotavap). The crude product is then subjected to fractional distillation, yielding 42.5 g (87%) of the desired product as a colourless oil.

EXAMPLE 3

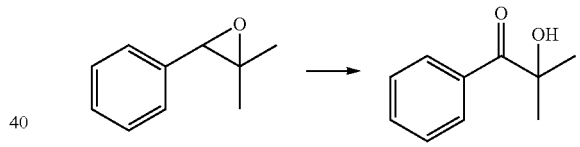

A mixture of 56 mg (0.25 mmol) Pd-acetate and 90 mg (0.25 mmol) bathocuproin in 50 mL of water is stirred for 24 h at room temperature. Subsequently, 741 mg (5 mmol) of the epoxide obtained in example 1 are added. The reaction mixture is stirred at 100° C. for 48 h under oxygen atmosphere. After evaporation, the residue is filtered over Alox and the crude product purified by chromatography (hexane:ethyl acetate 6:1), yielding 386 mg of the desired product.

EXAMPLE 4

Preparation of Epoxide

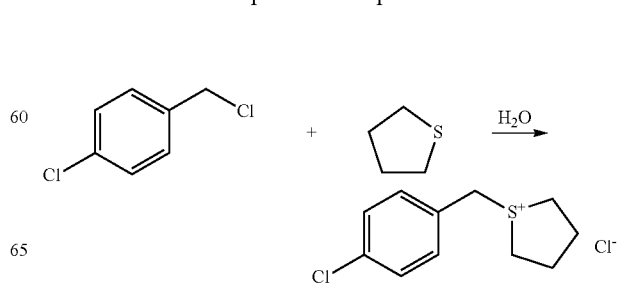

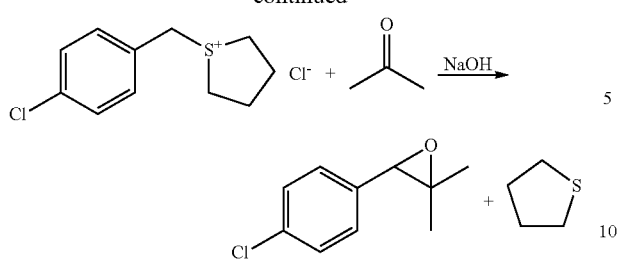

A mixture of 500 g (3.1 mol) of p-chlorobenzyl chloride and 282 g (3.1 mol) of tetrahydrothiophene in 0.78 L of water is heated at 85° C., whilst stirring well, until a homogeneous clear or slightly turbid single-phase solution has been obtained. The solution is then cooled to 20° C. and is slowly added dropwise to a reaction mixture consisting of 992 g of 50% sodium hydroxide solution (12.4 mol) and 720 g of acetone (12.4 mol) in 195 g of methanol. After the addition is complete, the reaction mixture is allowed to stand for 10 minutes until the phases have separated. The organic phase is separated off and the product obtained by distillation. 400 g of the desired product is obtained in the form of a clear colourless liquid.

EXAMPLE 5

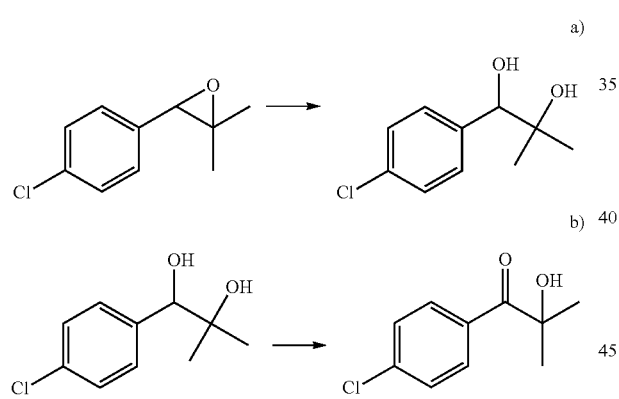

EXAMPLE 6

A mixture of 27 mg (0.12 mmol) of palladium acetate and 43 mg (0.12 mmol) of bathocuproine in 23 mL of water is stirred at room temperature for 24 hours. 420 mg (2.3 mmol) of epoxide (product of example 4) are then added and the reaction mixture is stirred at 100° C. under an oxygen atmosphere for 48 hours. The reaction mixture is concentrated by evaporation, the residue is filtered over Alox, and the desired product is isolated after chromatography on silica gel (hexane:ethyl acetate 6:1).

EXAMPLE 7

Preparation of Epoxide

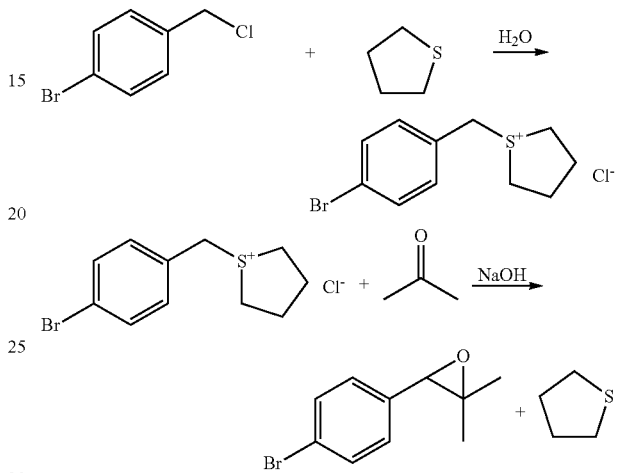

A mixture of 90 g (0.35 mol) of p-bromobenzyl chloride and 32 g (0.35 mol) of tetrahydrothiophene in 0.2 L of water is heated at 80° C., whilst stirring well, until a homogeneous clear or slightly turbid single-phase solution has been obtained. The solution is cooled to 60° C. and is slowly added dropwise to a reaction mixture, cooled to 15° C., consisting of 113 g of aqueous sodium hydroxide solution (50%, 1.41 mol) and 82 g of acetone (1.41 mol) in 30 mL of methanol. After the addition is complete, the reaction mixture is allowed to stand for about 10 minutes until the phases have separated. The organic phase is separated off and the product isolated by distillation. Yield: 58 g (73%) of epoxide in the form of a clear colourless liquid.

EXAMPLE 8

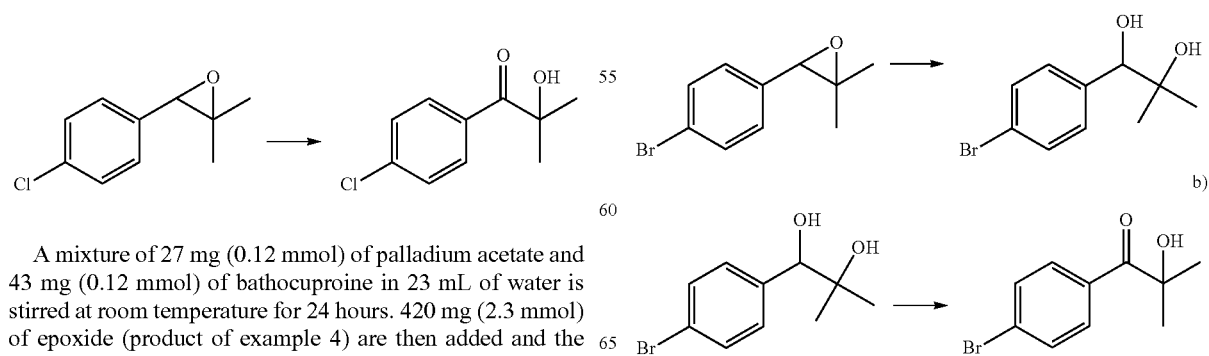

EXAMPLE 9

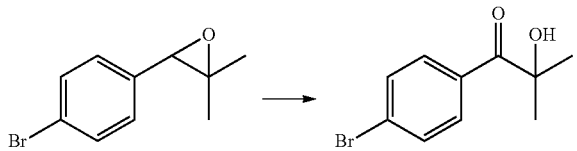

A mixture of 30 mg (0.135 mmol) of palladium acetate and 49 mg (0.135 mmol) of bathocuproine in 27 mL of water is stirred at room temperature for 24 hours. 609 mg (2.68 mmol) of epoxide (product of example 7) are then added and the reaction mixture is stirred at 100° C. under an oxygen atmosphere for 48 hours. The reaction mixture is concentrated by evaporation, the residue is filtered over Alox, and the desired product is obtained after chromatography on silica gel (hexane:ethyl acetate 6:1).

EXAMPLE 10

Preparation of Epoxide

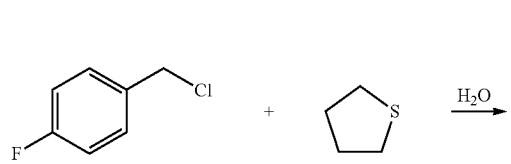

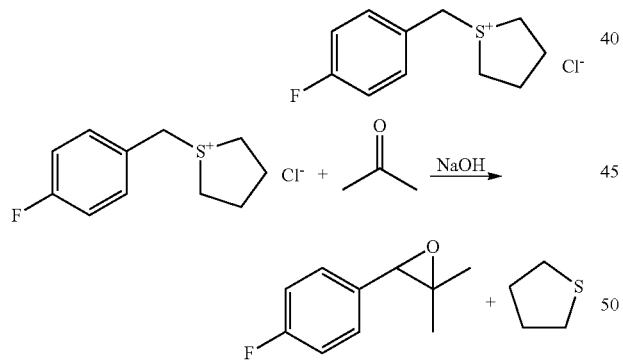

56 g (0.367 mol) of p-fluorobenzyl chloride, 33.4 g (0.367 mol) of tetrahydrothiophene and 0.1 L of water are heated at 85° C., whilst stirring well. After about 3 hours there is formed, from the two-phase reaction mixture, a homogeneous clear or slightly turbid single-phase solution of the corresponding sulphonium salt. The solution obtained is cooled to 25° C. and is slowly added, with stirring, to a mixture, cooled to 15° C., of 118 g of aqueous sodium hydroxide solution (50%, 1.47 mol) and 86 g of acetone (1.47 mol) in 25 mL of methanol. The mixture obtained is allowed to stand for about 10 minutes until the phases have separated; the organic phase is separated off and the product isolated by vacuum distillation. 45.2 g (74%) of the product are obtained in the form of a clear colourless liquid.

EXAMPLE 11

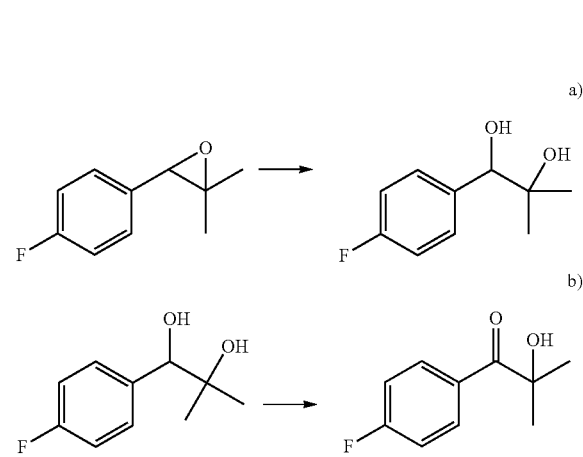

EXAMPLE 12

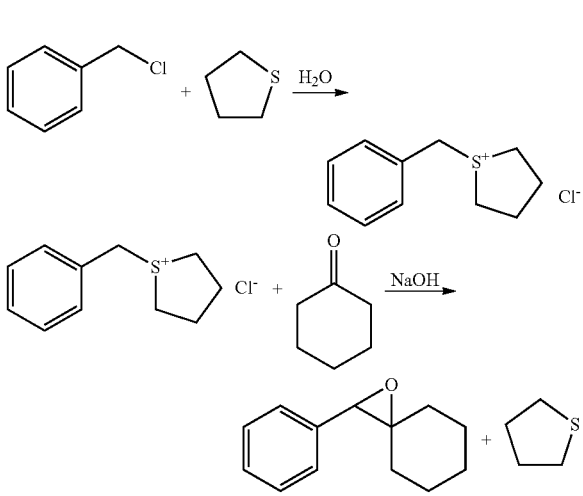

The reaction is carried out following the method of example 6, using the product of example 10 as starting material.

EXAMPLE 13

Preparation of Epoxide

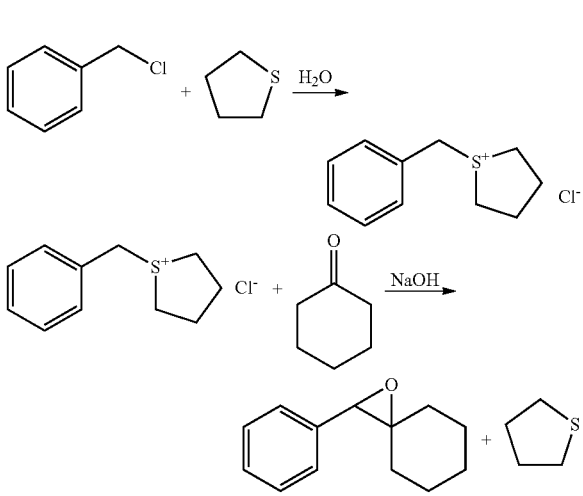

A mixture of 152 g (1.18 mol) of benzyl chloride, 108 g (1.18 mol) of tetrahydrothiophene and 0.225 L of water is stirred well at 85° C. until a homogeneous clear or slightly turbid single-phase solution of S-benzyltetrahydrothiophenium chloride has been obtained. The solution is cooled to 20° C. and is slowly added dropwise to a reaction mixture consisting of potassium hydroxide solution (prepared from 267 g (4.75 mol) of potassium hydroxide in 0.53 L of ice-water) and 467 g of cyclohexanone (4.75 mol) in 225 g of methanol. After the addition is complete, the reaction mixture is allowed to stand for 10 minutes until the phases have separated; the organic phase is separated off and subjected to fractional distillation. 181 g (80%) of 2-phenyl-1-oxa-spiro[2.5]octane are obtained in the form of a clear colourless oil.

EXAMPLE 14

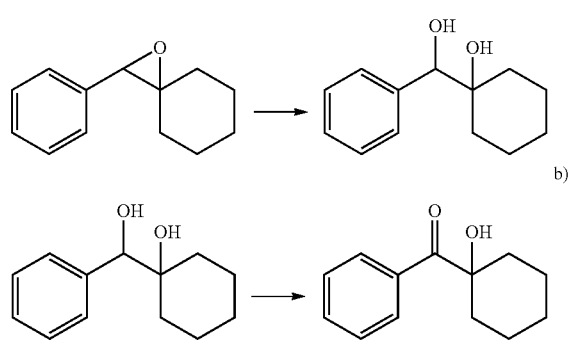

EXAMPLE 15

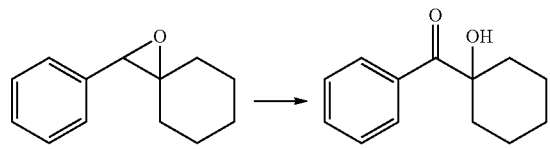 [SMILES: c1ccc(C2OC23CCCCC3)cc1 ; O=C(c1ccccc1)C1(O)CCCCC1]

A mixture of 0.112 g (0.5 mmol) of palladium acetate and 0.018 g (0.5 mmol) of bathocuproine in 100 mL of water is stirred at room temperature for 24 hours. 1.88 g (10 mmol) of epoxide (product of example 13) are then added and the reaction mixture is stirred at 100° C. under an oxygen atmosphere for 48 hours. After cooling to room temperature, the product is extracted twice using 150 mL of ethyl acetate each time. The combined organic phases are dried over sodium sulphate and concentrated by evaporation, and the crude product is chromatographed on silica gel (hexane:ethyl acetate 9:1). The desired product is obtained in the form of a light-yellow oil.

EXAMPLE 16

Preparation of Epoxide

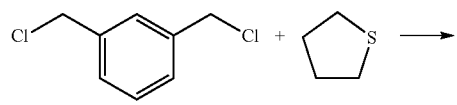

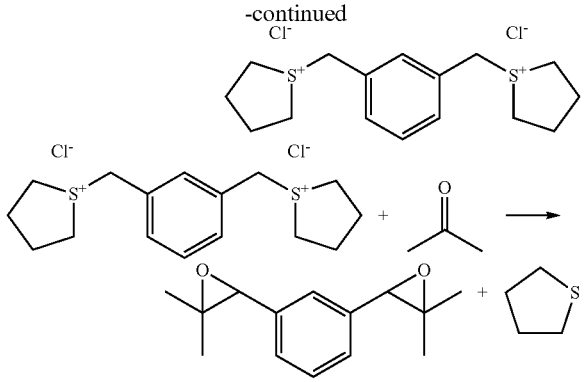

A mixture of 90 g (0.503 mol) of 1,3-bis(chloromethyl)benzene (α,α'-dichloro-m-xylene) and 91.4 g (1.0 mol) of tetrahydrothiophene in 0.18 L of water is heated at 85° C., whilst stirring well, until a homogeneous clear or slightly turbid single-phase solution has been obtained. The solution is cooled to room temperature and is slowly added dropwise, with stirring, to a reaction mixture of 320 g of aqueous sodium hydroxide solution (50%, 4.0 mol) and 233 g of acetone (4.0 mol) in 45 mL of methanol. After the addition is complete, the reaction mixture is allowed to stand for 10 minutes until the phases have separated. The organic phase is separated off and the product 1,3-bis-epoxybenzene obtained by distillation in the form of a yellow oil.

EXAMPLE 17

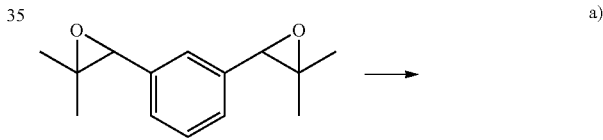

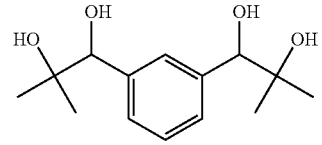

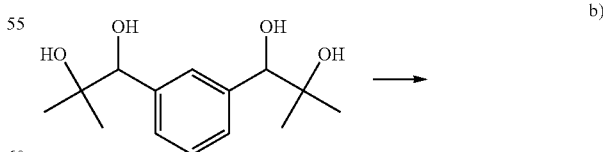

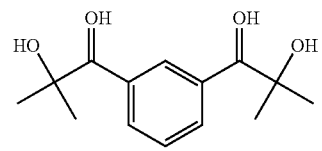

EXAMPLE 18

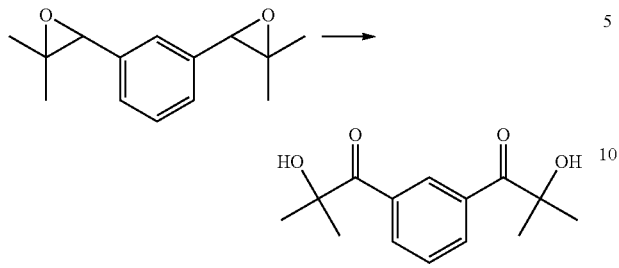

A mixture of 45 mg (0.2 mmol) of palladium acetate and 72 mg (0.2 mmol) of bathocuproine in 20 mL of water is stirred at room temperature for 24 hours. 437 mg (2.0 mmol) of epoxide (product of example 16) are then added and the reaction mixture is stirred at 100° C. under an oxygen atmosphere for 40 hours. After cooling to room temperature, the product is extracted three times using 50 mL of chloroform each time. The combined organic phases are dried over sodium sulphate and concentrated by evaporation, and the desired product is obtained after chromatography on silica gel (hexane:ethyl acetate 9:1).

The invention claimed is:

1. A process for the preparation of a α-hydroxyketone or α-aminoketone from 1,1-dicarbo substituted oxirane, wherein the 1,1-dicarbo substituted oxirane is a compound of the formula II

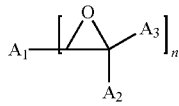

(II)

wherein n ranges from 1 to 4;

$A_1$, if n is 1, is carbocyclic aryl which is unsubstituted or substituted by OPr, $NR_9R_{10}$, carboxy, $COR_1$, $SO_2R_2$, halogen, nitro, CN, Aro, and/or by alkyl, alkoxy, alkenyl or alkenyloxy, each of which itself is unsubstituted or substituted by OPr, halogen, $NR_9R_{10}$, carboxy, Aro, $COR_1$, $SO_2R_2$, nitro, CN; or is carbocyclic aryl substituted by O—$R_8$—O—$SiR_{11}R_{12}R_{13}$;

or $A_1$ is alkyl, alkenyl, alkoxy, alkenyloxy, each of which is unsubstituted or substituted by OPr, halogen, $NR_9R_{10}$, Aro, $COR_1$, $OCOR_3$, $NR_9COR_3$, and/or, if having at least 3 carbon atoms, can be interrupted in a carbon-carbon single bond by O, $NR_9$, COO, $CONR_9$; or $A^1$ is hydrogen;

$A_1$, if n is 2, is Ar—$R_5$—Ar; or is a residue $R_{11}R_{12}Si(O—R_8—O—Ar)_2$; or $A_1$ is a direct bond;

$A_1$, if n is 3, is a residue $(Ar)_3—R_6$; or is a residue $R_{11}Si(O—R_8—O—Ar)_3$;

$A_1$, if n is 4, is a residue $(Ar)_4—R_7$;

$A_2$ and $A_3$ independently are alkyl, alkenyl, cycloalkyl, cycloalkenyl, aryl, alkylaryl, arylalkyl, cycloalkylalkyl, or one of said residues substituted by OPr, $NR_9R_{10}$, carboxy, $COR_1$, $SO_2R_2$, halogen, nitro, CN; and/or, if having at least 3 carbon atoms, are interrupted in a carbon-carbon single bond by O, $NR_9$, COO, $OCONR_9$, $CONR_9$;

or $A_2$ and $A_3$ together are $C_4$-$C_{11}$alkylene, -oxaalkylene, -azaalkylene or -alkenylene, each of which is unsubstituted or substituted by OPr, $NR_9R_{10}$, carboxy, $COR_1$, $SO_2R_2$, halogen, nitro, CN, and/or by alkyl, alkoxy, alkenyl, alkenyloxy, each of which itself is unsubstituted or substituted by OPr, $NR_9R_{10}$, carboxy, $COR_1$, $SO_2R_2$, halogen, nitro, CN;

Ar stands for a divalent carbocyclic aryl which is unsubstituted or substituted by OPr, $NR_9R_{10}$, carboxy, $COR_1$, $SO_2R_2$, halogen, nitro, CN, Aro, alkyl, alkoxy;

Aro stands for aryloxy which is unsubstituted or substituted by OPr, $NR_9R_{10}$, carboxy, $COR_1$, $SO_2R_2$, halogen, nitro, CN, alkyl, alkoxy, alkenyl, alkenyloxy;

Pr stands for hydrogen or a protecting group;

$R_1$ is hydrogen, OH, alkyl, alkenyl, cycloalkyl, cycloalkenyl, phenyl, alkylphenyl, alkoxyphenyl, alkoxy, alkenoxy, cycloalkoxy, cycloalkenoxy, phenoxy, alkylphenoxy, alkoxyphenoxy;

$R_2$ is OH, alkyl or alkoxy;

$R_3$ is alkyl, alkenyl, cycloalkyl, cycloalkenyl, phenyl, alkylphenyl, alkoxyphenyl;

$R_4$ and $R'_4$ independently are hydrogen, $C_1$-$C_{12}$alkyl or cyclohexyl;

$R_5$ is a direct bond; a heteroatomic spacer selected from —O—, —$NR_9$—, —S—, —SO—, $SO_2$—, CO, COO; $C_1$-$C_{18}$alkylene; $C_3$-$C_{18}$alkenylene; or $C_1$-$C_{18}$-alkylene interrupted or end-capped by —O—, —$NR_9$—, —S—, —SO—, $SO_2$—, CO, COO, $CONR_9$, $OCONR_9$, OCOO, cyclohexylene, phenylene and/or substituted by OPr or $NR_9R_{10}$; or $R_5$ is a tri- or tetravalent $C_3$-$C_{12}$alkyl moiety with 2 of its chemical bonds attached to one Ar and its $3^{rd}$ and, if present, $4^{th}$ chemical bond attached to the other Ar moiety;

$R_6$ is $C_2$-$C_{18}$-alkane-triyl optionally interrupted or end-capped by —O—, —$NR_9$—, —S—, —SO—, $SO_2$—, CO, COO, $CONR_9$, $OCONR_9$, OCOO, cyclohexylene, phenylene, and which is unsubstituted or substituted by OPr or $NR_9R_{10}$; or is $C_3$-$C_{18}$alkene-triyl;

$R_7$ is $C_2$-$C_{18}$-alkane-tetryl optionally interrupted or end-capped by —O—, —$NR_9$—, —S—, —SO—, $SO_2$—, CO, COO, $CONR_9$, $OCONR_9$, OCOO, cyclohexylene, phenylene, and which is unsubstituted or substituted by OPr or $NR_9R_{10}$; or is $C_4$-$C_{18}$alkene-tetryl;

$R_8$ is a divalent aliphatic or cycloaliphatic residue;

$R_9$ and $R_{10}$ independently are hydrogen, $C_1$-$C_{12}$alkyl, $C_1$-$C_{12}$alkyl substituted by OPr and/or $NR_4R'_4$, $C_5$-$C_{12}$cycloalkyl; or $R_9$ and $R_{10}$ are joined together to form a tetramethylene, pentamethylene, oxatetramethylene or oxapentamethylene moiety;

$R_{11}$, $R_{12}$ and $R_{13}$ independently are $C_1$-$C_{12}$alkyl or $C_1$-$C_{12}$alkoxy, which process comprises the steps of:

ii) reacting a sulphonium salt conforming to the formula

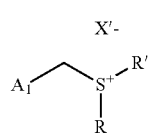

wherein R is alkyl of 1 to 20 carbon atoms, which is unsubstituted or substituted by $C_5$-$C_{12}$cycloalkyl or phenyl, and R' is as defined for R or is $C_5$-$C_{12}$cycloalkyl, phenyl, phenyl substituted by $C_1$-$C_{12}$alkyl; or R and R' together are penta- or hexamethylene, which may be substituted by $C_1$-$C_{12}$alkyl or phenyl;

$A_1$ is an aromatic organic carbon anchor group; and
$X'^-$ is a suitable anion;
with a ketone in presence of a base and a polar solvent, and then subsequently converting the 1,1-dicarbo substituted oxirane into an α-hydroxyketone or α-aminoketone,
wherein the α-hydroxyketone or α-aminoketone is of the formula I'

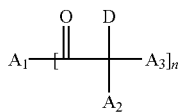

(I')

wherein
n ranges from 1 to 4;
$A_1$, if n is 1, is carbocyclic aryl which is unsubstituted or substituted by OPr, $NR_9R_{10}$, carboxy, $COR_1$, $SO_2R_2$, halogen, nitro, CN, Aro, and/or by alkyl, alkoxy, alkenyl or alkenyloxy, each of which itself is unsubstituted or substituted by OPr, halogen, $NR_9R_{10}$, carboxy, Aro, $COR_1$, $SO_2R_2$, nitro, CN; or is carbocyclic aryl substituted by O—$R_8$—O—$SiR_{11}R_{12}R_{13}$;
$A_1$, if n is 2, is Ar—$R_5$—Ar; or is a residue $R_{11}R_{12}Si(O—R_8—O—Ar)_2$;
$A_1$, if n is 3, is a residue $(Ar)_3$—$R_6$; or is a residue $R_{11}Si(O—R_8—O—Ar)_3$;
$A_1$, if n is 4, is a residue $(Ar)_4$—$R_7$;
$A_2$ and $A_3$ independently are alkyl, alkenyl, cycloalkyl, cycloalkenyl, aryl, alkylaryl, arylalkyl, cycloalkylalkyl, or one of said residues substituted by OPr, $NR_9R_{10}$, carboxy, $COR_1$, $SO_2R_2$, halogen, nitro, CN; and/or, if having at least 3 carbon atoms, are interrupted in a carbon-carbon single bond by O, $NR_9$, COO, $OCONR_9$, $CONR_9$;
or $A_2$ and $A_3$ together are $C_4$-$C_{11}$alkylene, -oxaalkylene, -azaalkylene or -alkenylene, each of which is unsubstituted or substituted by OPr, $NR_9R_{10}$, carboxy, $COR_1$, $SO_2R_2$, halogen, nitro, CN, and/or by alkyl, alkoxy, alkenyl, alkenyloxy, each of which itself is unsubstituted or substituted by OPr, $NR_9R_{10}$, carboxy, $COR_1$, $SO_2R_2$, halogen, nitro, CN;
Ar stands for a divalent carbocyclic aryl which is unsubstituted or substituted by OPr, $NR_9R_{10}$, carboxy, $COR_1$, $SO_2R_2$, halogen, nitro, CN, Aro, alkyl, alkoxy;
Aro stands for aryloxy which is unsubstituted or substituted by OPr, $NR_9R_{10}$, carboxy, $COR_1$, $SO_2R_2$, halogen, nitro, CN, alkyl, alkoxy, alkenyl, alkenyloxy;
Pr stands for hydrogen or a protecting group;
D is OH;
$R_1$ is hydrogen, OH, alkyl, alkenyl, cycloalkyl, cycloalkenyl, phenyl, alkylphenyl, alkoxyphenyl, alkoxy, alkenoxy, cycloalkoxy, cycloalkenoxy, phenoxy, alkylphenoxy, alkoxyphenoxy;
$R_2$ is OH, alkyl or alkoxy;
$R_3$ is alkyl, alkenyl, cycloalkyl, cycloalkenyl, phenyl, alkylphenyl, alkoxyphenyl;
$R_4$ and $R'_4$ independently are hydrogen, $C_1$-$C_{12}$alkyl or cyclohexyl;
$R_5$ is a direct bond; a heteroatomic spacer selected from —O—, —NR—, —S—, —SO—, $SO_2$—, CO, COO; $C_1$-$C_{18}$ alkylene; $C_3$-$C_{18}$ alkenylene; or $C_1$-$C_{18}$-alkylene interrupted or end-capped by —O—, —NR—, —S—, —SO—, $SO_2$—, CO, COO, $CONR_9$, $OCONR_9$, OCOO, cyclohexylene, phenylene and/or substituted by OPr or $NR_9R_{10}$; or $R_5$ is a tri- or tetravalent $C_3$-$C_{12}$alkyl moiety with 2 of its chemical bonds attached to one Ar and its $3^{rd}$ and, if present, $4^{th}$ chemical bond attached to the other Ar moiety;
$R_6$ is $C_2$-$C_{18}$-alkane-triyl optionally interrupted or end-capped by —O—, —$NR_9$—, —S—, —SO—, $SO_2$—, CO, COO, $CONR_9$, $OCONR_9$, OCOO, cyclohexylene, phenylene, and which is unsubstituted or substituted by OPr or $NR_9R_{10}$; or is $C_3$-$C_{18}$alkene-triyl;
$R_7$ is $C_2$-$C_{18}$-alkane-tetryl optionally interrupted or end-capped by —O—, —$NR_9$—, —S—, —SO—, $SO_2$—, CO, COO, $CONR_9$, $OCONR_9$, OCOO, cyclohexylene, phenylene, and which is unsubstituted or substituted by OPr or $NR_9R_{10}$; or is $C_4$-$C_{18}$alkene-tetryl;
$R_8$ is a divalent aliphatic or cycloaliphatic residue;
$R_9$ and $R_{10}$ independently are hydrogen, $C_1$-$C_{12}$alkyl, $C_1$-$C_{12}$alkyl substituted by OPr and/or $NR_4R'_4$, $C_5$-$C_{12}$cycloalkyl; or $R_9$ and $R_{10}$ are joined together to form a tetramethylene, pentamethylene, oxatetramethylene or oxapentamethylene moiety;
$R_{11}$, $R_{12}$ and $R_{13}$ independently are $C_1$-$C_{12}$alkyl or $C_1$-$C_{12}$alkoxy;
$R_{18}$ and $R_{19}$, independently, are selected from H, $C_1$-$C_4$alkyl, or are joined together to form a tetramethylene, pentamethylene, oxatetramethylene, oxapentamethylene, or to form an azatetramethylene or azapentamethylene moiety, wherein the nitrogen atom is unsubstituted or is substituted by $C_1$-$C_4$alkyl.

2. The process of claim 1, wherein
$A_1$, if n is 1, is phenyl which is unsubstituted or substituted by $C_1$-$C_{12}$alkyl, $C_1$-$C_{12}$alkoxy, $C_1$-$C_{12}$alkyl substituted by OPr, $C_2$-$C_{12}$alkoxy substituted by OPr; or is phenyl substituted by O—$R_8$—O—Si—$(CH_3)_3$;
$A_1$, if n is 2, is a residue phenylene-$R_5$-phenylene; or is a residue $(CH_3)_2Si(O—R_8—O$-phenylene$)_2$;
$A_1$, if n is 3, is a residue (phenylene)$_3$—$R_6$; or is a residue $CH_3Si(O—R_8—O$-phenylene$)_3$;
$A_1$, if n is 4, is a residue (phenylene)$_4$—$R_7$;
$A_2$ and $A_3$ independently are $C_1$-$C_4$alkyl, or together are pentamethylene;
$R_5$ is a direct bond; —O—; —$NR_9$—; CO; $C_1$-$C_{12}$alkylene; $C_1$-$C_4$-alkylene substituted by OPr or $NR_9R_{10}$; $C_2$-$C_4$alkylene interrupted by —O—, —$NR_9$—; or $R_5$ is a trivalent $C_3$-$C_{12}$alkyl moiety with 2 of its chemical bonds attached to one phenylene and its $3^{rd}$ chemical bond attached to the other phenylene moiety;
$R_6$ is $C_3$-$C_{18}$-alkane-triyl; or $C_3$-$C_{18}$alkane-triyl interrupted —O—, —$NR_9$—, COO, $CONR_9$, $OCONR_9$, OCOO; or is $C_3$-$C_{18}$alkene-triyl;
$R_7$ is $C_4$-$C_{18}$-alkane-tetryl; or $C_4$-$C_{18}$alkane-tetryl interrupted by —O—, —$NR_9$—, COO, $CONR_9$, $OCONR_9$, OCOO, phenylene, cyclohexylene; or is $C_4$-$C_{18}$alkene-tetryl;
$R_8$ is $C_2$-$C_{18}$-alkylene, or $C_3$-$C_{36}$alkylene interrupted by —O—, —$NR_9$—, COO, $CONR_9$, $OCONR_9$, OCOO, cyclohexylene;
$R_9$ and $R_{10}$ independently are hydrogen, $C_1$-$C_{12}$alkyl; or together are oxapentamethylene;
$R_{11}$, $R_{12}$ and $R_{13}$ independently are $C_1$-$C_4$alkyl.

3. The process of claim 1, wherein the 1,1-dicarbo substituted oxirane is subsequently
iii) hydrolyzed in the presence of an aqueous acid to form the corresponding dialcohol, iv) and the product obtained treated with an oxidizing agent selected from hypochlorite, hypobromite and hypervalent iodine reagents to form an α-hydroxyketone; or iii') subjected to aminolysis in the presence of a catalyst to form the corresponding aminoalcohol, wherein the catalyst is 2,2,6,6-tetramethylpiperidine-1-oxyl, iv) and the product obtained treated with an oxidizing agent selected from hypochlorite, hypobromite and hypervalent iodine reagents to form an α-aminoketone; or iii") subjected to aerobic oxidation in the presence of a transition metal catalyst to form an α-hydroxyketone.

4. The process of claim 3 for the preparation of an alpha-hydroxy ketone, where in step (iii) the reaction is carried out in presence of water or mixtures of water with an organic solvent;

and the acid is a protic acid selected from hydrogen halogenides, sulfonic acids, sulfuric acid, acidic hydrogen sulfates, phosphoric acids, carboxylic acids, acidic minerals;

and the temperature ranges from 40-100° C.

5. The process of claim 3, where in step (iv) the oxidizing agent is hypochlorite of lithium, sodium or potassium;

a catalyst is added in an amount ranging from 0.1 to 10 mol-% relative to the dialcohol or aminoalcohol, wherein the catalyst is 2,2,6,6-tetramethylpiperidine-1-oxyl; and the temperature during the oxidation step is kept within the range −10 to +15° C.

6. The process of claim 1, wherein $A_1$, if n is 1, is phenyl which is unsubstituted or substituted by OPr, $NR_9R_{10}$, carboxy, $COR_1$, $SO_2R_2$, halogen, nitro, CN, Aro; and/or by $C_1$-$C_{18}$alkyl, $C_1$-$C_{18}$alkoxy, $C_2$-$C_{18}$alkenyl or $C_2$-$C_{18}$alkenyloxy, each of which itself is unsubstituted or substituted by OPr, halogen, $NR_9R_{10}$, carboxy, Aro, $COR_1$, $SO_2R_2$, nitro, CN; or is phenyl substituted by O—$R_8$—O—$SiR_{11}R_{12}R_{13}$; or $A_1$ is $C_1$-$C_{18}$alkyl, $C_1$-$C_{18}$alkoxy, $C_2$-$C_{18}$alkenyl or $C_2$-$C_{18}$alkenyloxy, each of which is unsubstituted or substituted by OPr, halogen, $NR_9R_{10}$, Aro, $COR_1$, $OCOR_3$, $NR_9COR_3$, and/or, if having at least 3 carbon atoms, can be interrupted in a carbon-carbon single bond by O, $NR_9$, COO, $CONR_9$;

$A_1$, if n is 2, is Ar—$R_5$—Ar; or is a residue $R_{11}R_{12}Si(O$—$R_8$—O—Ar$)_2$; or $A_1$ is a direct bond;

$A_1$, if n is 3, is a residue (Ar)$_3$—$R_6$; or is a residue $R_{11}Si(O$—$R_8$—O—Ar$)_3$;

$A_1$, if n is 4, is a residue (Ar)$_4$—$R_7$;

$A_2$ and $A_3$ independently are $C_1$-$C_{18}$alkyl; $C_2$-$C_{18}$alkenyl; $C_4$-$C_{12}$cycloalkyl; $C_5$-$C_{12}$cycloalkenyl;

phenyl; $C_7$-$C_{15}$-phenylalkyl; $C_7$-$C_{15}$cyclohexylalkyl; or one of said residues substituted by OPr, $NR_9R_{10}$, COOH, $COR_1$, $SO_2R_2$, halogen, nitro, CN; and/or, if having at least 3 carbon atoms, are interrupted in a carbon-carbon single bond by O, $NR_9$, COO, $OCONR_9$, $CONR_9$;

or $A_2$ and $A_3$ together are $C_4$-$C_{11}$alkylene, -oxaalkylene, -azaalkylene or -alkenylene, each of which is unsubstituted or substituted by OPr, $NR_9R_{10}$, carboxy, $COR_1$, $SO_2R_2$, halogen, nitro, CN, and/or by a residue selected from $C_1$-$C_{18}$alkyl, $C_1$-$C_{18}$alkoxy, $C_2$-$C_{18}$alkenyl, $C_2$-$C_{18}$alkenyloxy, each of which itself is unsubstituted or substituted by OPr, amino, carboxy, $COR_1$, $SO_2R_2$, halogen, nitro, CN;

Ar is phenylene, which is unsubstituted or substituted by OPr, $NR_9R_{10}$, carboxy, $COR_1$, $SO_2R_2$, halogen, nitro, CN, $C_1$-$C_{18}$alkyl, $C_1$-$C_{18}$alkoxy, $C_2$-$C_{18}$alkenyl, $C_2$-$C_{18}$alkenyloxy, phenoxy;

$R_1$ is hydrogen, OH, $C_1$-$C_{18}$alkyl; $C_2$-$C_{18}$alkenyl; $C_4$-$C_{12}$cycloalkyl; $C_5$-$C_{12}$cycloalkenyl;

phenyl, $C_7$-$C_{18}$alkylphenyl, $C_1$-$C_{18}$alkoxyphenyl, $C_1$-$C_{18}$alkoxy, $C_2$-$C_{18}$alkenoxy, $C_4$-$C_{12}$cycloalkoxy, $C_5$-$C_{12}$cycloalkenoxy, phenoxy, $C_7$-$C_{18}$alkylphenoxy, $C_7$-$C_{18}$alkoxyphenoxy;

$R_2$ is OH, $C_1$-$C_{18}$alkyl or $C_1$-$C_{18}$alkoxy;

$R_3$ is $C_1$-$C_{18}$alkyl; $C_2$-$C_{18}$alkenyl; $C_4$-$C_{12}$cycloalkyl; $C_5$-$C_{12}$cycloalkenyl;

phenyl, $C_7$-$C_{18}$alkylphenyl, $C_1$-$C_{18}$alkoxyphenyl;

$R_5$ is a direct bond; a heteroatomic spacer selected from —O—, —NR—, —S—, —SO—, $SO_2$—, CO, COO; $C_1$-$C_{18}$alkylene; $C_3$-$C_{18}$alkenylene; or $C_1$-$C_{18}$-alkylene interrupted or end-capped by —O—, —NR—, —S—, —SO—, $SO_2$—, CO, COO, $CONR_9$, $OCONR_9$, OCOO, cyclohexylene, phenylene and/or substituted by OPr or $NR_9R_{10}$; or $R_5$ is a tri- or tetravalent $C_3$-$C_{12}$alkyl moiety with 2 of its chemical bonds attached to one Ar and its $3^{rd}$ and, if present, $4^{th}$ chemical bond attached to the other Ar moiety;

$R_6$ is $C_2$-$C_{18}$-alkane-triyl optionally interrupted or end-capped by —O—, —NR—, —S—, —SO—, $SO_2$—, CO, COO, $CONR_9$, $OCONR_9$, OCOO, cyclohexylene, phenylene, and which is unsubstituted or substituted by OPr or $NR_9R_{10}$; or is $C_3$-$C_{18}$alkene-triyl;

$R_7$ is $C_2$-$C_{18}$-alkane-tetryl optionally interrupted or end-capped by —O—, —NR—, —S—, —SO—, $SO_2$—, CO, COO, $CONR_9$, $OCONR_9$, OCOO, cyclohexylene, phenylene, and which is unsubstituted or substituted by OPr or $NR_9R_{10}$; or is $C_4$-$C_{18}$alkene-tetryl;

$R_8$ is $C_1$-$C_{18}$-alkylene, or $C_3$-$C_{36}$alkylene interrupted by —O—, —NR—, —S—, —SO—, $SO_2$—, CO, COO, $CONR_9$, $OCONR_9$, OCOO, cyclohexylene;

$R_9$ and $R_{10}$ independently are hydrogen, $C_1$-$C_{12}$alkyl, $C_1$-$C_{12}$alkyl substituted by OPr, cyclohexyl; or $R_9$ and $R_{10}$ are joined together to form a pentamethylene or oxapentamethylene moiety;

$R_{11}$, $R_{12}$ and $R_{13}$ independently are $C_1$-$C_{12}$alkyl or $C_1$-$C_{12}$alkoxy.

7. The process of claim 6, wherein $A_1$, if n is 1, is phenyl which is unsubstituted or substituted by $C_1$-$C_{12}$alkyl, $C_1$-$C_{12}$alkoxy, $C_1$-$C_{12}$alkyl substituted by OPr, $C_2$-$C_{12}$alkoxy substituted by OPr; or is phenyl substituted by O—$R_8$—O—Si—(CH$_3$)$_3$;

$A_1$, if n is 2, is a residue phenylene-$R_5$-phenylene; or is a residue (CH$_3$)$_2$Si(O—$R_8$—O-phenylene)$_2$;

$A_1$, if n is 3, is a residue (phenylene)$_3$—$R_6$; or is a residue CH$_3$Si(O—$R_8$—O-phenylene)$_3$;

$A_1$, if n is 4, is a residue (phenylene)$_4$—$R_7$;

$A_2$ and $A_3$ independently are $C_1$-$C_4$alkyl, or together are pentamethylene;

$R_5$ is a direct bond; —O—; —$NR_9$—; CO; $C_1$-$C_{12}$alkylene; $C_1$-$C_4$-alkylene substituted by OPr or $NR_9R_{10}$; $C_2$-$C_4$alkylene interrupted by —O—, —$NR_9$—; or $R_5$ is a trivalent $C_3$-$C_{12}$alkyl moiety with 2 of its chemical bonds attached to one phenylene and its $3^{rd}$ chemical bond attached to the other phenylene moiety;

$R_6$ is $C_3$-$C_{18}$-alkane-triyl; or $C_3$-$C_{18}$alkane-triyl interrupted —O—, —$NR_9$—, COO, $CONR_9$, $OCONR_9$, OCOO; or is $C_3$-$C_{18}$alkene-triyl;

$R_7$ is $C_4$-$C_{18}$-alkane-tetryl; or $C_4$-$C_{18}$alkane-tetryl interrupted by —O—, —$NR_9$—, COO, $CONR_9$, $OCONR_9$, OCOO, phenylene, cyclohexylene; or is $C_4$-$C_{18}$alkene-tetryl;

$R_8$ is $C_2$-$C_{18}$-alkylene, or $C_3$-$C_{36}$alkylene interrupted by —O—, —NR$_9$—, COO, CONR$_9$, OCONR$_9$, OCOO, cyclohexylene;

$R_9$ and $R_{10}$ independently are hydrogen, $C_1$-$C_{12}$alkyl; or together are oxapentamethylene;

$R_{11}$, $R_{12}$ and $R_{13}$ independently are $C_1$-$C_4$alkyl.

* * * * *